United States Patent
Goldhor et al.

(10) Patent No.: US 10,067,093 B2
(45) Date of Patent: Sep. 4, 2018

(54) DECOMPOSING DATA SIGNALS INTO INDEPENDENT ADDITIVE TERMS USING REFERENCE SIGNALS

(71) Applicant: Speech Technology & Applied Research Corporation, Bedford, MA (US)

(72) Inventors: Richard S. Goldhor, Belmont, MA (US); Keith Gilbert, Berlin, MA (US); Joel MacAuslan, Nashua, NH (US)

(73) Assignees: Richard S. Goldhor, Belmont, MA (US); Speech Technology & Applied Research Corporation, Bedford, MA (US)

( * ) Notice: Subject to any disclaimer, the term of this patent is extended or adjusted under 35 U.S.C. 154(b) by 195 days.

(21) Appl. No.: 15/160,860

(22) Filed: May 20, 2016

(65) Prior Publication Data

US 2016/0341701 A1 Nov. 24, 2016

Related U.S. Application Data

(60) Provisional application No. 62/164,465, filed on May 20, 2015.

(51) Int. Cl.
| | |
|---|---|
| *H03F 1/26* | (2006.01) |
| *G01N 29/14* | (2006.01) |
| *G01N 29/44* | (2006.01) |
| *G01N 29/46* | (2006.01) |
| *G06F 11/30* | (2006.01) |

(52) U.S. Cl.
CPC ........ *G01N 29/14* (2013.01); *G01N 29/4472* (2013.01); *G01N 29/46* (2013.01); *G01N 2291/044* (2013.01)

(58) Field of Classification Search
CPC ...................................................... G01N 29/14
See application file for complete search history.

(56) References Cited

U.S. PATENT DOCUMENTS

| | | |
|---|---|---|
| 2006/0072767 A1 | 4/2006 | Zhang |
| 2010/0128897 A1 | 5/2010 | Saruwatari |
| (Continued) | | |

OTHER PUBLICATIONS

M. Akil and C. Serviere, "Seperabililty of convolutive mixtures based on Wiener filtering and mutual information criterion," in Signal Processing conference, 2006 14th European, 2006, pp. 1-4.*

(Continued)

*Primary Examiner* — Phuong Huynh
(74) *Attorney, Agent, or Firm* — Blueshift IP, LLC; Robert Plotkin

(57) ABSTRACT

A system processes data signals consisting of sums of independent signal terms in order to generate one or more of those terms. The generated terms are computed using a set of reference signals to construct alternative support sets, whose images are computed on the data signals. Computed images that are independent of the residue of the data signal minus the image are identified as independent signal terms, as are the residues. These initial signal terms are used to compute additional terms. Identified terms from different data signals are organized into independent slices, and slices whose terms are supported by sets of reference signals are associated with those supporting sets.

20 Claims, 20 Drawing Sheets

(56) References Cited

U.S. PATENT DOCUMENTS

2013/0294608 A1 11/2013 Yoo
2017/0230654 A1* 8/2017 Jung .................. H04N 19/102

OTHER PUBLICATIONS

M. Akil and C. Serviere, "Separability of convolutive mixtures based on Wiener filtering and mutual information criterion," in Signal Processing Conference, 2006 14th European, 2006, pp. 1-4.
R. Aichner, H. Buchner, and W. Kellermann, "Convolutive Blind Source Separation for Noisy Mixtures," in Speech and Audio Processing in Adverse Environments, E. Hänsler and G. Schmidt, Eds. Berlin, Heidelberg: Springer Berlin Heidelberg, 2008, pp. 469-524.
Cover, T. M., and Joy A. Thomas, "Elements of Information Theory" Wiley Series in Telecommunications. New York: Wiley, 1991. p. 18ff.
Golub, Gene H., and Charles F. Van Loan "Matrix Computations" 3rd ed. Johns Hopkins Studies in the Mathematical Sciences. Baltimore: Johns Hopkins University Press, 1996. Chapter 5, p. 230 ff.
Matsuoka, K. "Minimal Distortion Principle for Blind Source Separation," 4:2138-43. Soc. Instrument & Control Eng. (SICE), 2002. doi:10.1109/SICE.2002.1195729.
Matsuoka, Kiyotoshi, and Satoshi Nakashima. "Minimal Distortion Principle for Blind Source Separation." In Proc. Int. Conf. Independent Component Analysis and Blind Signal Separation. Rome, 2001.
Aichner, R, H Buchner, F Yan, and W Kellermann. "A Real-Time Blind Source Separation Scheme and Its Application to Reverberant and Noisy Acoustic Environments." Signal Processing 86, No. 6 (Jun. 2006): 1260-77. doi:10.1016/j.sigpro.2005.06.022.
Goldhor, Richard. "Sensor Image-Based Environmental Listening Assistant," NIH SBIR Grant No. R43 DC015416, Mar. 15, 2016.

* cited by examiner

DECOMPOSING DATA SIGNALS INTO INDEPENDENT ADDITIVE TERMS USING REFERENCE SIGNALS

STATEMENT AS TO FEDERALLY SPONSORED RESEARCH

This invention was made with Government support under NIH SBIR Grant R44-DC011668. The Government has certain rights in the invention.

CROSS-REFERENCE TO RELATED APPLICATIONS

This application is related to the following patent application, which is incorporated by reference herein:
U.S. patent application Ser. No. 13/933,060, filed on Jul. 1, 2013, entitled, "Signal Source Separation Partially Based on Non-Sensor Information."

BACKGROUND

In many common signal transmission environments, multiple signal sources are active at the same time. (For instance, in the real world, many acoustic sources in the environment may be simultaneously generating sounds.) A receiver (such as a listener) often would like to attend to a single signal source, but any sensor (e.g. microphone) in the environment typically responds to a mixture of sources. As indicated schematically in FIG. 1, each component of such a sensor's response corresponds to some source, delayed by the propagation time between that source and the sensor, and further filtered by echoes, radiation characteristics of the sources, and so forth. We call such a component a sensor image of its source.

It has been considered useful to be able to recover the underlying source signals from the available response mixtures, so that a listener could listen to each signal source separately. This is the source separation problem.

In a very important and common version of the source separation problem, the radiated signals of the underlying sources are not observable in any way. That is to say, they cannot be detected, measured, or recorded in isolation. Rather, the only available relevant information is the response signals generated by the sensors (e.g. microphones) that are present in the environment. The signals from those sensors (the "response mixtures," "sensor mixtures," or simply "mixtures") can be detected, captured, and processed.

From a signal processing perspective, the situation may be modeled as shown in FIG. 2. In this model it is assumed that the observable signals m are composed of convolutive mixtures of the unknown sources s. The relationship between the hidden source signals and the observable mixtures are defined by a hidden "mixing matrix" H. An important signal processing challenge is to estimate those underlying but hidden sources by processing the observed sensor responses to create Source Images. This is referred to as the Blind Source Separation (BSS) problem.

A distinct and separate problem is to determine the component sensor images of each source. Note that, in general, none of the sensor images of a source will be identical to the corresponding hidden source signal. Nor will one of the sensor images of a source be identical to another image of the same source. Instead, each sensor image constitutes an independent view of its source. Because there are many signal processing systems that either require or can take advantage of multiple independent images of a signal source, particularly if each image can be associated with a specific sensor, it would be particularly advantageous to decompose every sensor signal into its constituent sensor images.

SUMMARY

A system processes data signals consisting of sums of independent signal terms in order to generate one or more of those terms. The generated terms are computed using a set of reference signals to construct alternative support sets, whose images are computed on the data signals. Computed images that are independent of the residue of the data signal minus the image are identified as independent signal terms, as are the residues. These initial signal terms are used to compute additional terms. Identified terms from different data signals are organized into independent slices, and slices whose terms are supported by sets of reference signals are associated with those supporting sets.

Other features and advantages of various aspects and embodiments of the present invention will become apparent from the following description and from the claims.

DETAILED DESCRIPTION

Figure 1:
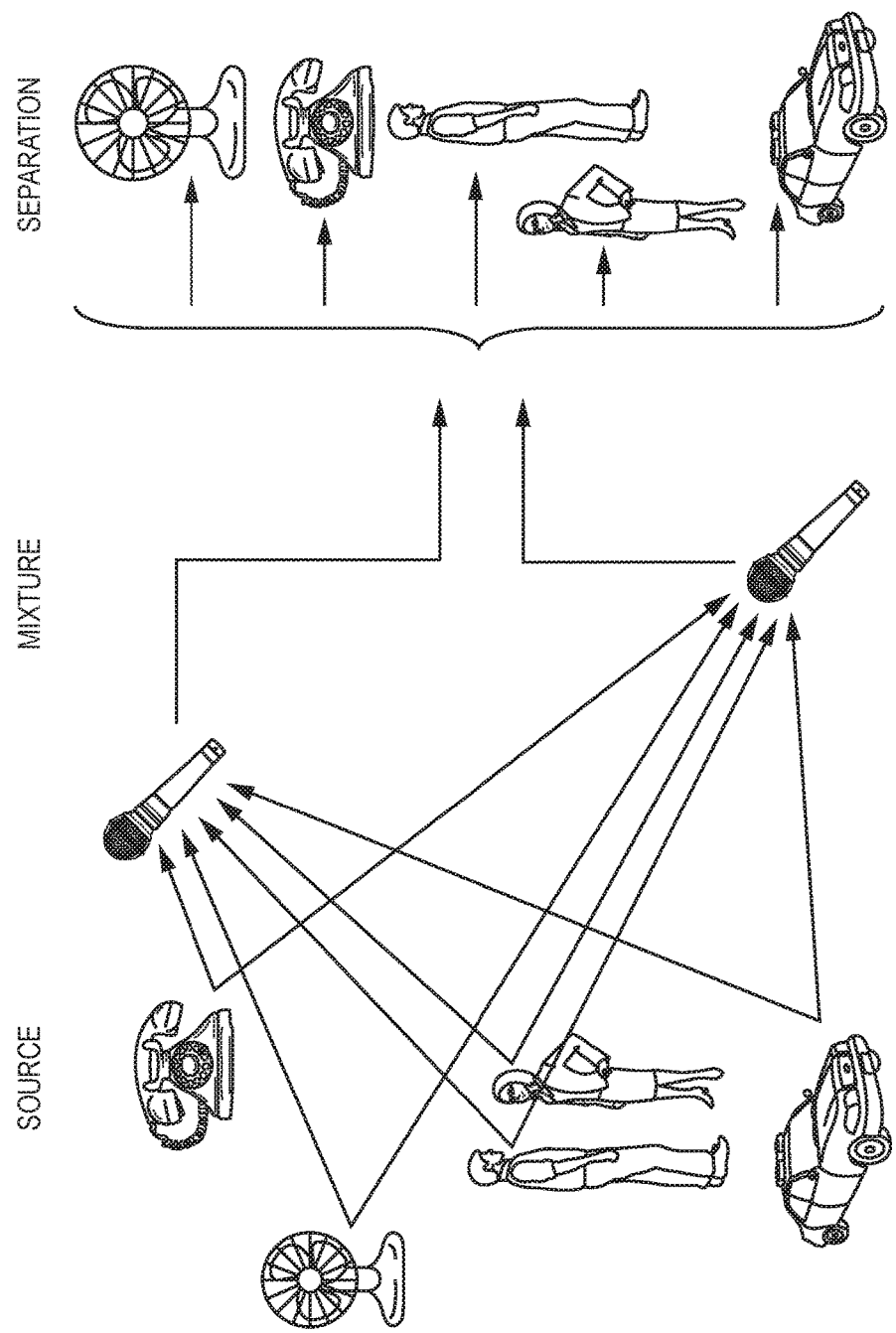
FIG. 1 is a diagram illustrating the response of a sensor to a mixture of sources in the environment.
Figure 2:
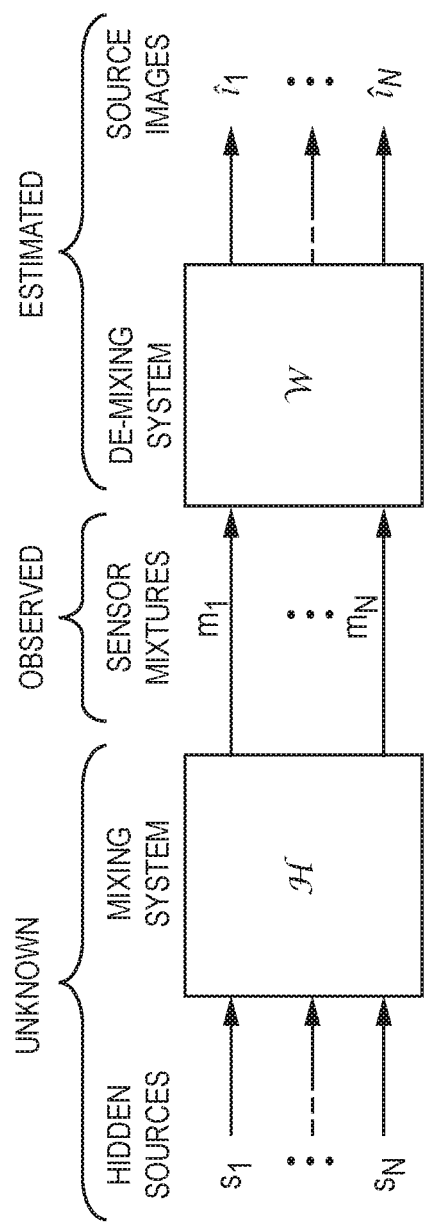
FIG. 2 is a diagram illustrating a model of sensor responses.

U.S. patent application Ser. No. 13/933,060 discloses a system for blind source separation that is referred to herein as the Acoustic Component Enhancement System Blind Source Separation algorithm (ACES BSS). Like many state-of-the-art BSS algorithms, certain embodiments of ACES BSS require at least as many sensor signals as there are active source signals. Certain embodiments of ACES BSS assume that the hidden source signals are mutually uncorrelated, non-stationary, and non-white.

In the traditional BSS problem statement, the goal of the signal processing to be performed is to estimate the hidden source signals. However, this goal is itself problematic. In general, there are logical and mathematical limitations to what BSS algorithms can achieve. Note that the sources are truly hidden, and in general no pristine source signal is directly observable. Indeed, in many scenarios, including common acoustic environments, the very concept of a specific set of hidden source signals is ontologically suspect.

In these situations, the characterization of the sources as "hidden" actually masks a deeper problem: those signals are not well defined. This may be true, curiously enough, even though a BSS algorithm generates well-behaved estimates of the "hidden source signals." This is possible because, in general, the power of an estimated source is different by an unknown amount from the power of the original hidden signal, the order of output estimates is typically unrelated to any particular enumeration of the input signals (the "permutation ambiguity"), the estimated source is time-shifted by an arbitrary amount relative to the original, and the spectral power profile of the estimate and its original is generally different. For this reason, each output of the BSS algorithm is referred to herein as a source image, building on the metaphoric understanding of images as being recognizable reproductions of some original (the hidden source signal), but differing in size, orientation, etc. A source image is any signal that is related to the putative hidden source signal of a particular signal source by a convolution kernel.

In fact, a source signal that is referred to as "hidden" actually is not any particular signal at all. Rather, it can best be considered to be an entire equivalence class of perfectly coherent signals. Thus, in a situation in which there are N simultaneously active sources, the computational situation can best be understood as a search for the definition of N equivalence classes, each Source Equivalence Class (SEC) corresponding to one of the active sources.

In this understanding of the BSS problem, each of the N estimated source images generated by the BSS algorithm is best understood as an estimate of some arbitrary member of one of the Source Equivalence Classes. Once any of the signals in an SEC is specified, all of the other signals in that class can, in theory, be generated, because any two signals in an SEC are related to each other via a finite length convolution kernel called an image kernel (and sometimes informally referred to as a "weight"). Given any member signal, there is another signal in the SEC corresponding to each possible convolution kernel.

Note that there are no image kernels capable of mapping a member of one SEC to a member of another SEC. This is because all members of one SEC are incoherent with all members of all other SECs. As a result, the expected value of a kernel defined by their ratios would have zero energy.

It will be understood that one of the members of each SEC might be regarded in some sense as the original "hidden source signal." But that hidden member cannot, in general, be identified without imposing additional constraints on the computational problem. And, in many cases, the hidden source signal cannot be identified because it is, in the absence of any such defensible constraints, not well defined.

It is true that the hidden source member of the SEC can be defined, or at least a narrower subset of the SEC containing the hidden source member can be defined, if additional constraints are imposed by the physical situation or the statement of the problem to be solved. For example, if the physical locations of all of the signal sources and sensors are specified, the members of the SEC that might qualify as the original signal can be constrained. Much current work on the BSS problem takes the approach of attempting to better define the original source signal by imposing additional situational or computational constraints, and working through their computational consequences. Such systems are often identified as Blind Deconvolution and Blind System Identification systems.

Embodiments of the invention disclosed herein are based on a different approach. Embodiments of the present invention include methods and systems for decomposing one or more data signals, drawn from a set of data signals. This set of data signals is referred to herein as "the data set." Each data signal is modeled as being composed of an unweighted instantaneous sum of independent signals referred to herein as independent signal terms, or "ISTs."

Each IST is itself modeled as a linear weighted mixture of one or more independent unknown source signals. This means that an IST is a sum of one or more hidden signals, each of which may be filtered by an arbitrary linear filter. The linear filtering of each source may, for example, take the form of a simple scalar amplification. In this "instantaneous" case, the linear filter is a simple gain factor (such as a unitary gain), and the linear filtering process that forms the IST may be a multiply-and-sum function. Alternatively, the mixing process may be fully "convolutive," in which case the linear filters have arbitrary impulse responses, and the linear weighting function may be modeled as a convolution of impulse responses with source signals, the weighted mixture elements being added together to form the IST.

The data signal itself consists of either a single IST, or an unweighted instantaneous sum of independent ISTs. Although the source signals and their filter characteristics are "hidden" (i.e., unknown and unobservable), under appropriate circumstances these additive ISTs can be determined by decomposing a data signal using techniques described below. Certain embodiments of this invention involve identifying ISTs from which the signals in a data set are composed. Certain embodiments of this invention include methods and systems for ascertaining useful properties of those ISTs.

The methods for decomposing data signals described herein employ one or more reference signals, which together comprise a reference set. The same reference set is employed for decomposing all of the data signals in a data set. In brief, the signals in the reference set are used to decompose each signal in the data set into separate parts, some of which are identified as valid ISTs, and others as not being valid ISTs—that is, not being any independent linear mixture of one or more of the hidden sources from which the data signal was formed. Using methods disclosed herein, valid ISTs are identified, and used to guide further decomposition and analysis.

Any well-formed signal may be employed as a reference signal, although some signals are inherently more useful as reference signals than others. It turns out that linear mixtures of the hidden sources from which the ISTs of data signals are constructed make useful reference signals, and that linearly filtered versions of the ISTs themselves make particularly useful reference signals.

Reference signals and data signals may take many forms, such as acoustic signals, or digital or analog audio signals resulting from microphone responses, electronic devices, etc. Signals may also be electrical in nature, arising from, for example, natural systems (e.g. bioelectrical signals) or engineered systems (e.g. electromagnetic equipment). Alternatively, for example, such signals may be ordered sequences of data values generated by numerical computing equipment.

Particularly useful reference signals may be constructed or identified in many ways. For example, external knowledge may be employed to establish a hypothesis that a selected signal is an IST of a data signal, and on the basis of that hypothesis the selected signal may be chosen as a reference signal. For example, if the response signals of a set of microphones comprise the data set, then the input signal to a loudspeaker in the vicinity of the microphones may be identified as one of the reference signals.

Alternatively, for example, reference signals may be generated from the data signals themselves. For instance, a Blind Source Separation (BSS) algorithm may be used to generate a set of reference signals from the data signals, as described, for example, in the above-referenced U.S. patent application Ser. No. 13/933,060. As another example, a "beamforming" algorithm may be used to generate one or more reference signals. All of the reference signals in a reference set may be generated using a single method, such as a BSS algorithm, or different reference signals in the reference set may be generated in different ways. The utility of the methods and systems disclosed herein does not depend on any particular method of generating reference signals.

Similarly, data signals may be constructed or identified in many ways. A data signal may, for example, represent an observable (that is, measurable) quantity in the real world, such as the output voltage of a sensor. As one example, the output signal of an acoustic microphone is a useful type of data signal, and the output signals from a set of microphones are an example of a useful data set.

Typically, digitally sampled signal values $x[k]$ are known to within some accuracy, generally represented as the variance of errors or uncertainties about $x[k]$. Often a single scalar value v can be determined that characterizes the variance of the entire signal. Testing whether signal values are different from zero then amounts to testing whether those values differ from 0 by significantly more than this known variance would predict, for a specified level of significance a, determined by the specifics of the situation.

We can make this determination by computing S, the sum of the squared signal values divided by v. We then determine, for this value of S, the tabulated or computed value P(S) of the cumulative of ChiSq[N], the chi-squared distribution with N degrees of freedom, where N is the number of samples in the signal. We accept a signal as being non-zero when P(S) is greater than $(1-\alpha)$. Values of P(S) that are smaller than $(1-\alpha)$ indicate that any overall non-zero signal, if present at all, is not detectable (by this test), given the known level of uncertainties in the $x[k]$. In these cases we consider the signal to be effectively zero.

To identify two signals as effectively equal, we subtract one from the other and determine whether this difference is effectively zero, using the same criteria as above.

The correlation of two signals u and v (at zero time lag) is measured as the integral of the product of u and the conjugate of v. Two signals whose correlation is zero or close to zero are said to be uncorrelated or decorrelated. The power of the sum of two signals perfectly decorrelated at zero time lag equals the sum of the power of the two signals.

The coherence of two signals u and v is measured as the mean over all frequencies f of the mean squared coherence function MSC(u, v, f), where MSC(u, v, f) is equal to the squared magnitude of the cross-power spectrum of u and v at f, divided by the product of the spectral powers of u and v at f. [See Kay, S. M. Modern Spectral Estimation. Englewood Cliffs, N.J.: Prentice-Hall, 1988, pp. 453-455.] Two signals whose coherence is zero or close to zero are said to be incoherent. Two signals whose coherence is one or close to one are said to coherent.

It is worth noting that signal incoherence is a more stringent condition than perfect decorrelation at zero time lag. That is, two signals may be perfectly decorrelated at zero time lag, but not mutually incoherent. However, all pairs of mutually incoherent signals are perfectly decorrelated at all time lags.

If and only if all pairs of signals in a reference set, data set, and other signal set are incoherent, the set is said to be orthogonal. If a signal is incoherent with each member of a set of signals, the signal is said to be orthogonal with the set, and vice versa. If all members of a first set of signals are orthogonal with a second set, the first set and the second set are orthogonal.

To determine whether two signals are effectively orthogonal, we align them by optionally shifting one of them relative to the other so that the peak of their cross-correlation function occurs at zero lag, and measure their coherence C (see above). We accept two signals as orthogonal if C is smaller than a specified context-dependent value such as 0.1, and fully coherent if C is greater than another context-dependent value such as 0.85.

If a set of N signals are not mutually orthogonal, they can be transformed into a set of M orthonormal basis signals (for M≤N) that is both orthogonal and normalized, forming an M-dimensional signal space. Among other techniques, the well-known Gram-Schmidt Orthogonal Process (see, e.g., Golub, G. and C. van Loan, *Matrix Computations*, 1996, John Hopkins Press) can be used to generate the basis signals. This new set of signals resembles the old set (e.g., each member of the old set can be formed as a linear combination of the new signals).

As described below, there are advantages and disadvantages to orthogonalizing either or both the reference set and the data sets. With the data set in particular, it must be noted that, in general, the basis signals in the orthogonalized data set are linear combinations of the original data signals. If those data signals were chosen because of extraneous properties, those properties might not apply to the orthogonalized signals. In other words, it is the set that is orthogonalized, not the individual signals in the set.

By way of example, if the data set represents the response of microphones in an acoustic environment, each microphone records the acoustic field at a particular location. If those signals are orthogonalized, the new signals do not, in general, represent the acoustic field in any physical location.

Two signals are said to be statistically independent at first order (i.e., considering only the relationship between single data values rather than pairs, triplets, etc.) if the values of one signal provide no information about the values of the other signal. Various measures of statistical independence are in common use. For instance, the mutual information MI between two signals is a convenient measure of their statistical dependence, so the value I equal to one minus the mutual information between the two signals, normalized by the maximum of the two signals marginal entropy, can be used as a numerical measure of their statistical independence (see Cover & Thomas, Elements of Information Theory, Wiley, 1991, p. 18ff). We accept two signals as independent if I is greater than a specified context-dependent value such as 0.8.

It is worth noting that statistical independence is a more stringent condition than incoherence. That is, two signals may be mutually incoherent but still not independent. However, all statistically independent signals are mutually incoherent.

It is useful to introduce the general concept of the quality of partition (or partition quality) between two arbitrary signals. The more similar two signals are, the less well they are partitioned. The less similar they are, the better they are partitioned. The partition quality between two signals can be objectively measured, and reported as a "QoP" real value which ranges between zero and one. Two identical signals have a QoP value of zero. Two fully partitioned signals have a QoP value of one.

Commonly, the partition quality of two signals is interpreted as the degree of statistical independence of those signals, and a standard measure of statistical independence (such as the mutual information-based measure given above) is employed as the QoP value. Measures of signal independence other than mutual information can be used to measure quality of partition. For example, signal coherence can be used to measure the quality of partition. However, statistical independence is often a particularly felicitous choice for quality of partition, because tests for statistical independence are generally sensitive to the presence of a common component in two mixtures, even when the two mixtures are themselves orthogonal (incoherent).

A reference set as a whole, and each distinct non-empty subset of that reference set, is said to constitute a support set that can be used to decompose any data signal into an image of the support set on the data signal, and a residue equal to the data signal minus the image. Both the image and the residue are themselves signals, and may be mixtures. Commonly, the residue of a decomposition may itself be a linear mixture, and may be further decomposed using the techniques described herein. The image may also be a mixture subject to further decomposition.

Depending upon the signals comprising the support set and the data signal, either the image or the residue may be effectively equal to the data signal itself. If the image is effectively equal to the data signal, we say that the decomposition of the Data Signal supported by that support set is inclusive. (In this case, the residue will be effectively zero.) If the residue is effectively equal to the data signal, we say that the decomposition of the data signal supported by that support set is exclusive. (In this case, the image will be effectively zero.) The decomposition of a reference set or signal on a data signal will be exclusive if and only if the reference set or signal is orthogonal to the data signal. Alternatively, neither the image nor the residue may be effectively equal to the data signal, in which case the decomposition is neither inclusive nor exclusive.

It is useful to measure the partition quality of image and residue pairs. If either the image or residue is effectively zero, and the other signal is not, their QoP is one. If the image and residue of a non-inclusive, non-exclusive decomposition have a QoP value effectively equal to one, then the decomposition of the data signal by that support set is a partitioning decomposition; otherwise, it is a blurring decomposition. The partition quality of a signal or set of signals onto a data signal is equal to the QoP of the image and residue of that signal or set onto that data signal.

It is worth noting that any image and its residue are incoherent, regardless of whether the decomposition that formed those signals is partitioning or not. In other words, all decompositions of a data signal into an image and a residue create an incoherent image-residue pair, but not all image-residue pairs are independent.

The image and residue of a partitioning decomposition of a data signal are ISTs of the data signal. We call the support set of that decomposition a partitioning reference set for that data signal. If an individual signal generates a partitioning decomposition of a data signal, we call that signal a partitioning signal for that data signal.

The image of a support set onto a designated signal (such as a data signal) is computed as the linear convolutive mixture of the signals in the support set that minimizes the mean square error between that mixture and the designated signal. Note that this optimal mixture may be instantaneous. The residue of a support set on a designated signal is computed as the designated signal minus the image of the support set on that designated signal, so the sum of the image and residue equals the designated signal. The image and the residue are uncorrelated, so the sum of their power equals the power of the designated signal.

If a reference set is orthogonal, the set of images of each signal in the reference set on any designated signal will be mutually orthogonal, and the sum of the power of those images will be equal to the power of the sum of the images. This is true even if some of the reference signals are incoherent with the designated signal, because the power of images of incoherent reference signals on the designated signal will be effectively zero. Furthermore, the power of the sum of the images will be equal to the power of the joint image of the reference set on the designated signal, which is equal to the power of the mixture minus the power of the residue of that joint image. Note, however, that the mutual orthogonality of the individual reference signal images onto a designated signal does not guarantee that those images are ISTs of the designated signal—that is, that the reference signals are partitioning signals for the designated signal.

If a signal is composed of an unweighted sum of independent terms (ISTs), for any first IST of that signal, its residue (that is, the signal minus the IST) is a second IST of the signal. It may be that either of those ISTs may be further decomposed into additional independent ISTs called sub-ISTs. The residue of a sub-IST of an IST (that is, the IST minus any sub-IST) is also a sub-IST.

As a signal is decomposed, using a set of reference signals, into independent ISTs, that signal and each of its ISTs can have associated with it a base set of reference signals. The base set of a signal is the minimal subset of the reference set for which some linear mixture of the reference signals in the base set is identical to the signal. It is worth noting that:

all members of the base set of a signal are members of the reference set;

the base set of an image is the support set of the partitioning decomposition that produced the image;

the base set of an IST includes the union of the base sets of all identified sub-ISTs of that IST;

the base set of a signal includes the union of the base sets of the image-residue pair of any partitioning decomposition of that signal; and the base sets of mutual sub-ISTs of an IST are disjoint.

That is, any reference signal that is a member of the base set of an IST is a member of the base set of no more than one sub-IST of the IST.

Figure 3:
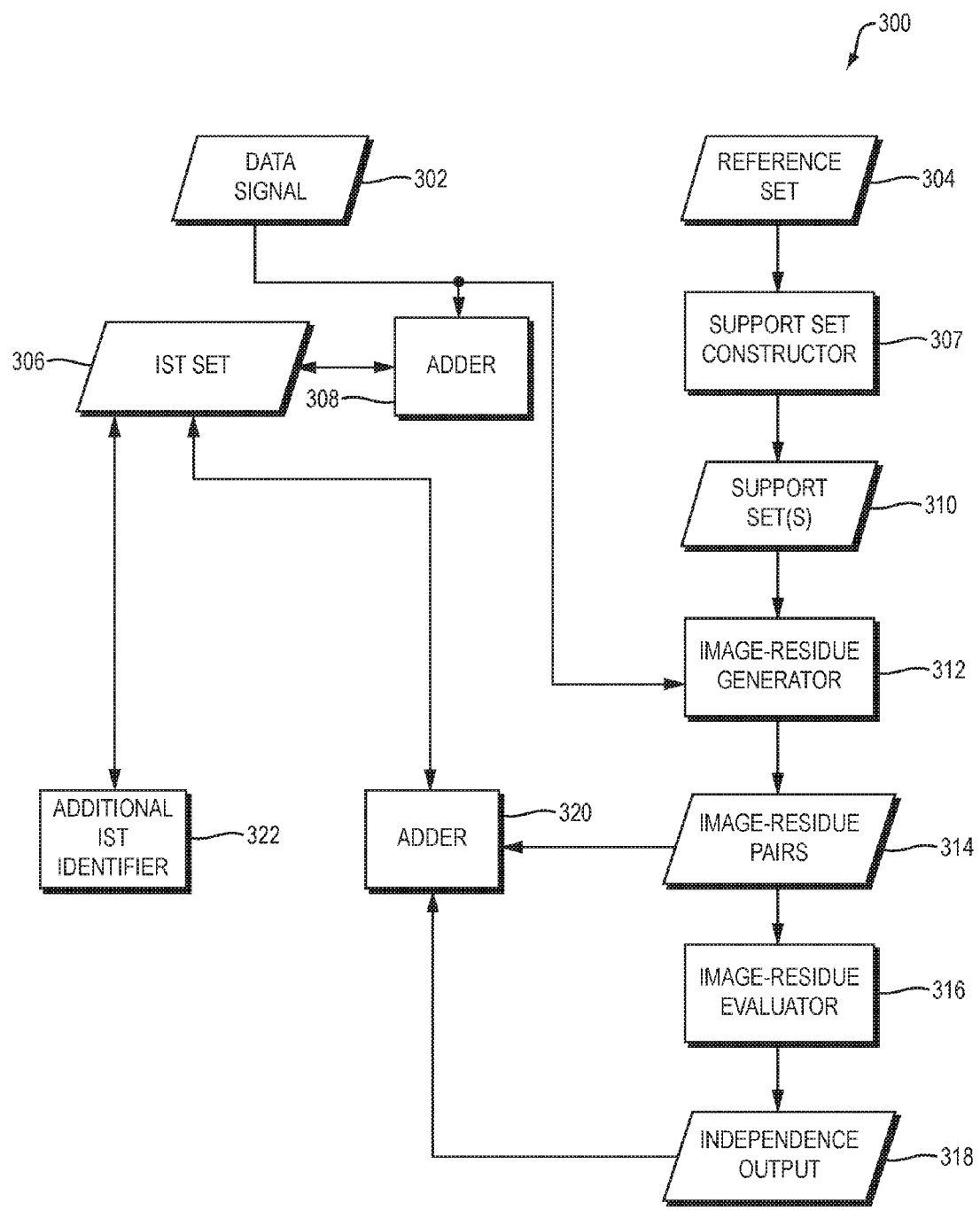
FIG. 3 is a dataflow diagram of a system for identifying independent signal terms (ISTs) of a data signal, given the data signal and a reference set, according to one embodiment of the present invention.
Figure 4A:
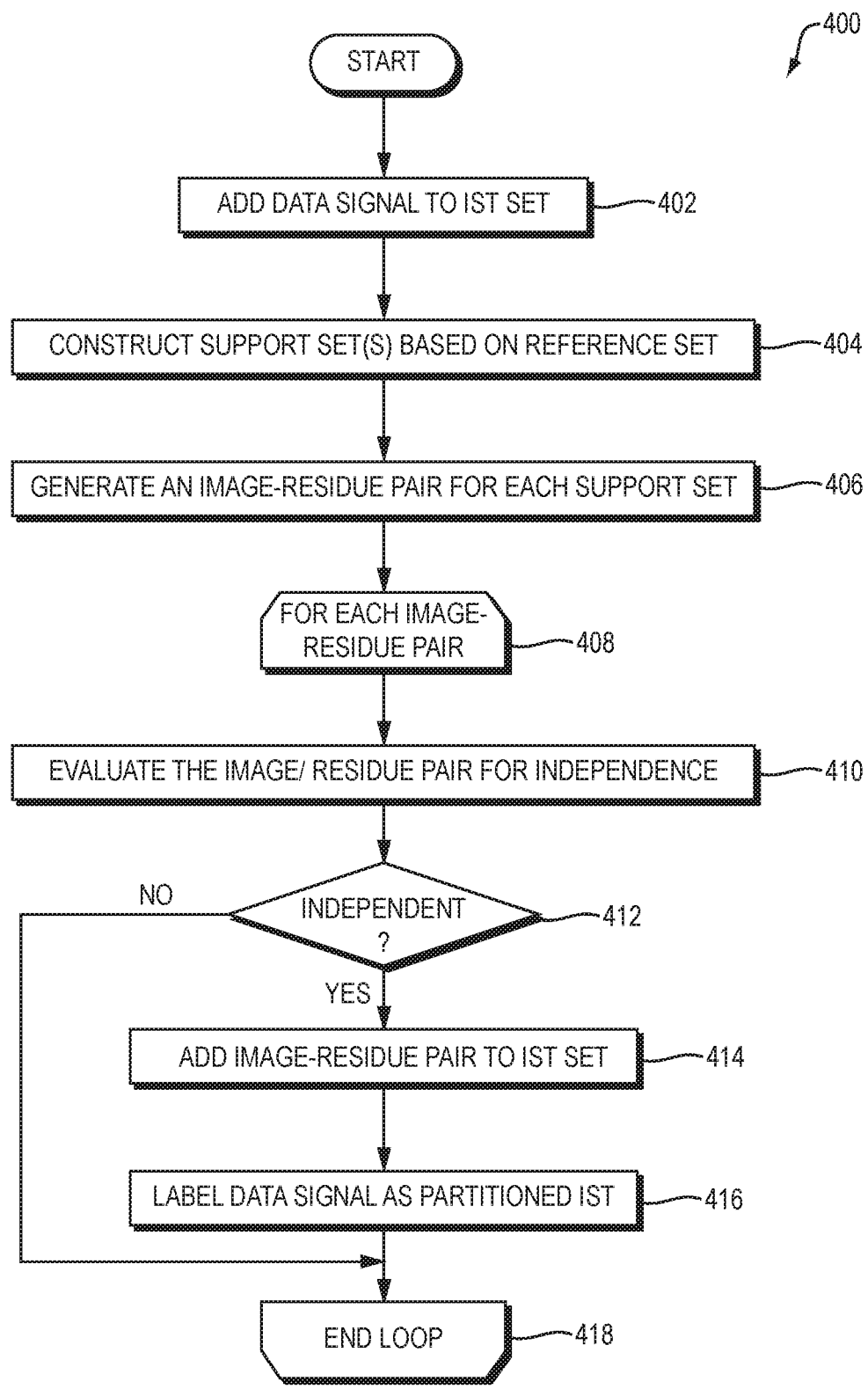
FIGS. 4A-4B are flowcharts of methods performed by the system of FIG. 3 according to one embodiment of the present invention.

Referring to FIG. 3, a dataflow diagram is shown of a system 300 for identifying ISTs of a data signal 302, given the data signal 302 and a reference set 304, according to one embodiment of the present invention. Referring to FIG. 4A, a flowchart is shown of a method 400 performed by the system 300 of FIG. 3 according to one embodiment of the present invention.

The ISTs identified by the system 300 and method 400 of FIGS. 3 and 4A may be considered to be members of an IST set 306, which is associated with the data signal 302 and its reference set 304. Not every data signal/reference set combination yields a non-trivial data set. The data signal 302 and the reference set 304 in FIG. 3, for example, may or may not yield a non-trivial data set. For instance, if the data signal 302 is orthogonal to the reference set 304, then the reference set cannot be used to decompose the data signal 302, and the IST set 306, at the conclusion of the method 400, is just the data signal 302 itself. Likewise, if none of the support sets that can be formed from the reference set 304 partition the data signal, then the reference set 304 cannot be used to decompose the data signal 302, and the IST set 306, at the conclusion of the method 400, is just the data signal 302 itself.

The system 300 and method 400 may construct the IST set 306 as follows. Initially, the IST set 306 includes no members. Then an adder 308 adds the data signal 302 to the IST set 306, as a result of which the IST set 306 includes only the data signal 302 (FIG. 4A, operation 402).

The reference set 304 defines a set of possible support sets, that set consisting of the reference set 304 and all distinct non-empty subsets of the reference set 304. A support set constructor 307 constructs at least one support set 310 based on the reference set 304 (FIG. 4A, operation 404). The support set(s) 310 may, for example, be all possible support sets that may be constructed based on the reference set 304.

An image-residue generator 312 generates (e.g., computes), for each of the support set(s) 310, the image and residue defined by that support set on the data signal 302, by performing a decomposition of the data signal 302 based on that support set into the image and residue. The result is a set of one or more image-residue pairs 314, each of which corresponds to a distinct one of the support set(s) 310 (FIG. 4A, operation 406). For each of the image-residue pairs 314 (FIG. 4A, operations 408 and 418), an image-residue evaluator 316 evaluates the image-residue pair for independence (FIG. 4A, operation 410), thereby producing independence output 318 indicating, for each of the image-residue pairs 314, whether the image and residue in the image-residue pair are independent of each other. The evaluation of each of the image-residue pairs 314 for independence in operation 410 effectively determines whether the decomposition that produced that image-residue pair was a partitioning decomposition.

If the image-residue evaluator 316 determines that a particular image-residue pair is independent (i.e., if the decomposition that generated the image-residue pair is determined to be a partitioning decomposition) (FIG. 4A, operation 412), then an adder 320 adds that image-residue pair to the IST set 306 (FIG. 4A, operation 414), and labels the data signal 302 as a partitioned IST (FIG. 4A, operation 416).

Figure 4B:
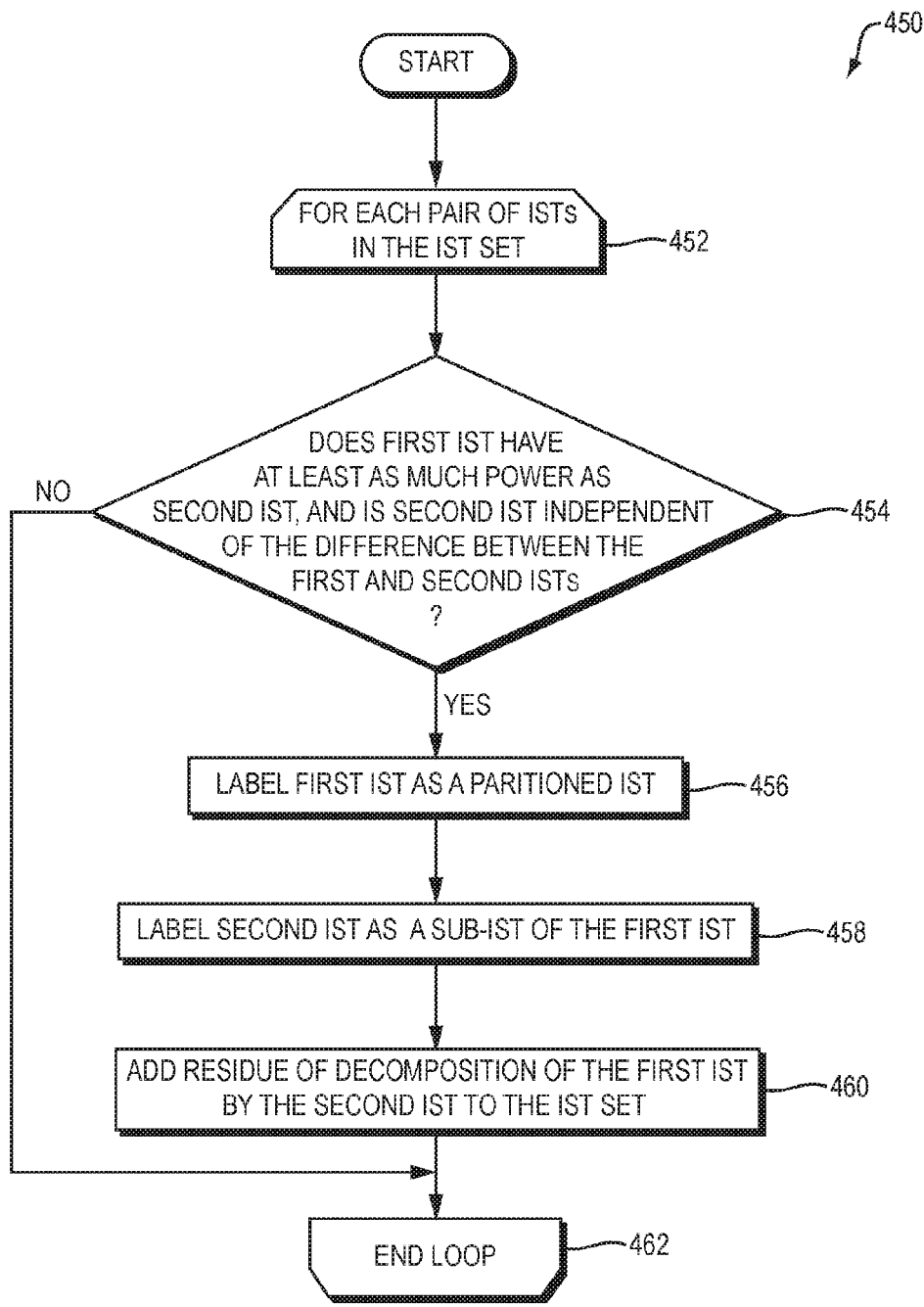

The data signal 302 may be labeled as a partitioned IST in any of a variety of ways, such as by storing data (e.g., in the IST set 306), indicating that the data signal 302 is a partitioned IST. Although FIG. 4B shows the data signal 302 being labeled as a partitioned IST each time an image-residue pair is determined to be independent, this is not required. Alternatively, for example, the data signal 302 may be labeled as a partitioned IST only once, e.g., in response to the first time that an image-residue pair is determined to be independent.

In a second phase of processing, additional ISTs may be identified and added to the IST set 306 by iteratively identifying additional partitioning decompositions of the data signal 302 using ISTs that were previously identified, and which therefore are already in the IST set 306. More specifically, and referring now to the method 450 of FIG. 4B, an additional IST identifier 322 may enter a loop over each pair of ISTs in the IST set 306 (FIG. 4B, operation 452), where each such pair includes a first IST and a second IST, and determine, for each such pair of ISTs, whether: (i) the first IST has at least as much power as the second IST; and (ii) the second IST is independent of the difference between the first IST and the second IST (FIG. 4B, operation 454). If both conditions (i) and (ii) are satisfied for the pair of ISTs, then the additional IST identifier 322: (1) labels the first IST as a partitioned IST (FIG. 4B, operation 456); (2) labels the second IST as a sub-IST of the first IST (FIG. 4B, operation 458); and (3) adds a residue of the decomposition of the first IST by the second IST to the IST set 306 (FIG. 4B, operation 460). Note that the different between the first IST and the second IST is the residue of the decomposition of the first IST by the second IST.

The loop initiated in operation 452 may repeat any number of times (FIG. 4B, operation 462). As a result, the method 450 of FIG. 4B may cause any number of additional available ISTs to be identified and added to the IST set 306. Upon conclusion of the method 450 of FIG. 4B, every IST for which an image-residue pair, or sub-ISTs, have been identified will have been labeled a partitioned IST. Every IST in the IST set that is not labeled as a partitioned IST is considered to be labeled an irreducible IST.

Figure 5:
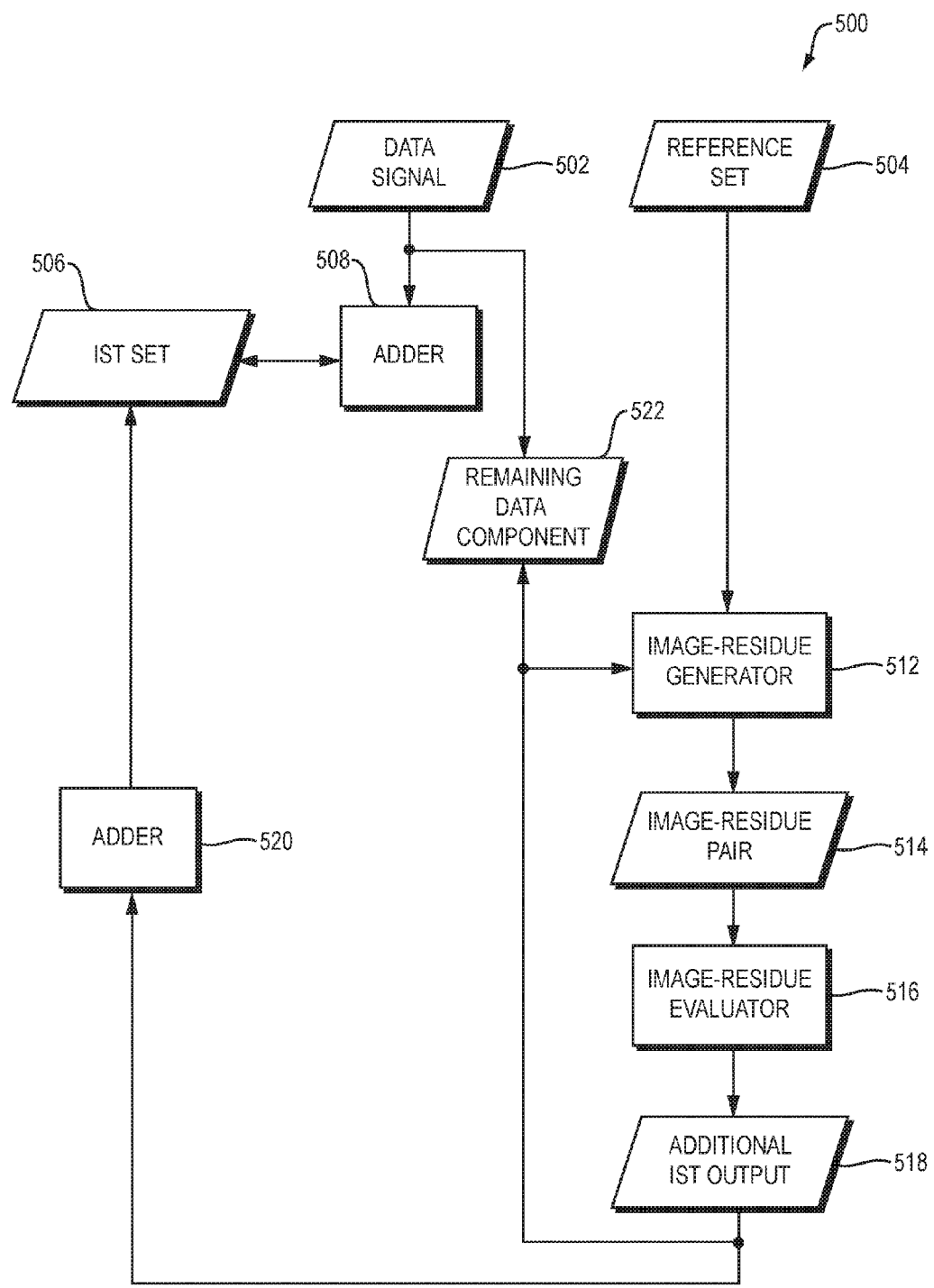
FIG. 5 is a dataflow diagram of a system for identifying independent additive ISTs of a data signal, given the data signal and a reference set, when all of the reference signals in the reference set are mutually orthogonal, according to one embodiment of the present invention.
Figure 6:
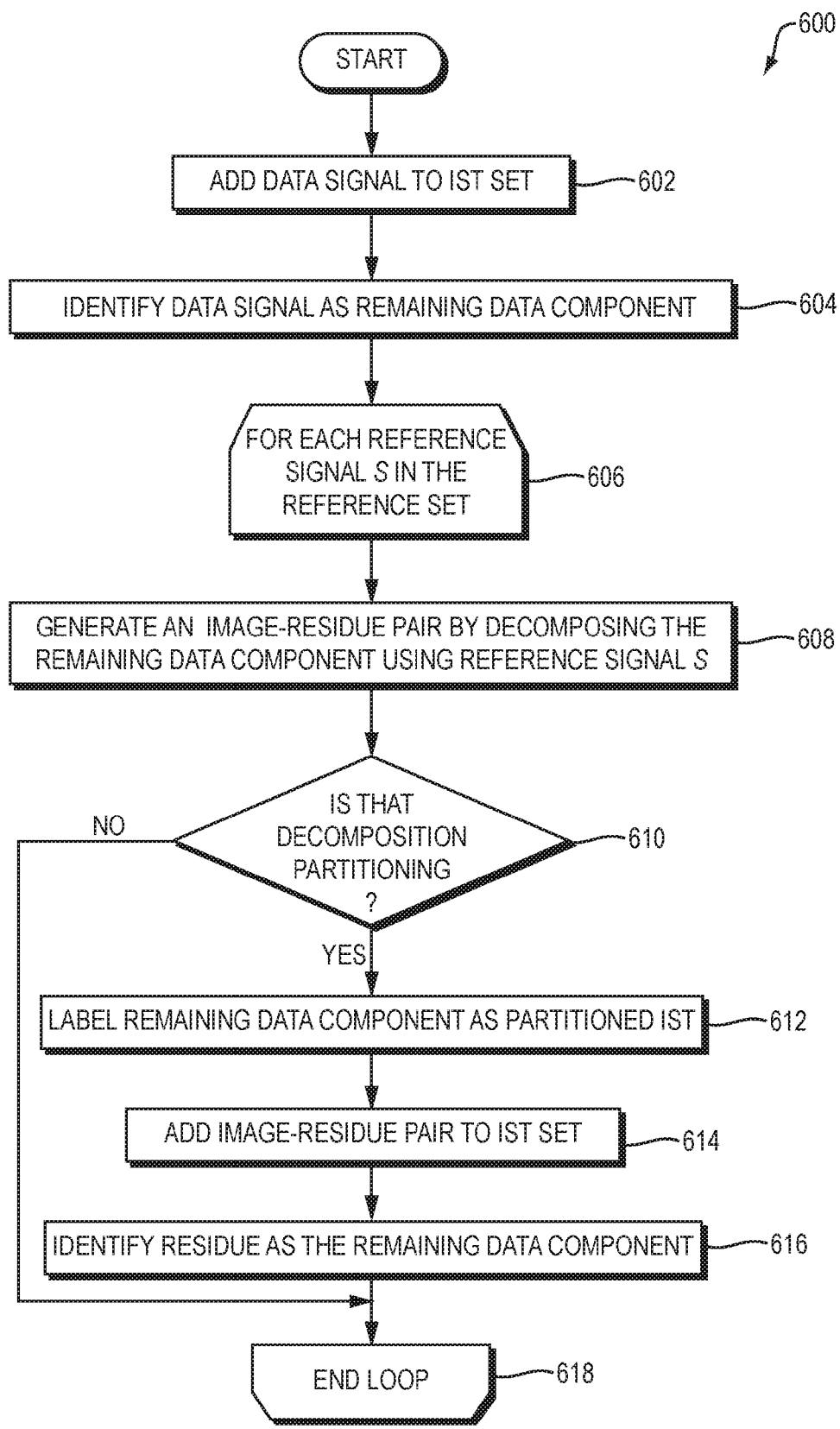
FIG. 6 is a flowchart of a method performed by the system of FIG. 5 according to one embodiment of the present invention.

If all of the reference signals in the reference set 304 are mutually independent, then an alternative method to the ones illustrated in FIGS. 3 and 4A-4B may be used to create the IST set for any data set. This alternative method is illustrated in FIGS. 5 and 6. More specifically, FIG. 5 is a dataflow diagram of a system 500 for identifying independent additive ISTs of a data signal 502, given the data signal 502 and a reference set 504, when all of the reference signals in the reference set 504 are mutually orthogonal, according to one embodiment of the present invention. Referring to FIG. 6, a flowchart is shown of a method 600 performed by the system 500 of FIG. 5 according to one embodiment of the present invention.

The system 500 and method 600 may construct the IST set 506 as follows. Initially, the IST set 506 includes no members. Then an adder 508 adds the data signal 502 to the IST set 506, as a result of which the IST set 506 includes only the data signal 502 (FIG. 6, operation 602). The method 600 identifies the data signal 502 as the "remaining data component" (FIG. 6, operation 604). The system 500 enters a loop over each reference signal S in the reference set 504 (FIG. 6, operation 606). An image-residue generator 512 generates (e.g., computes), the image and residue defined by reference signal S on the remaining data component, by performing a decomposition of the remaining data component based on reference signal S into the image and residue (FIG. 6, operation 608). The result is an image-residue pair 514 corresponding to the remaining data component.

An image-residue evaluator 516 determines whether the decomposition performed in operation 608 is a partitioning decomposition (FIG. 6, operation 610). If the image-residue evaluator 516 finds that it is, then: (1) the image-residue evaluator 516 labels the remaining data component as a partitioned IST (FIG. 6, operation 612); and (2) an adder 520 adds the image and residue in the image-residue pair 514 to the IST set 506, based on output 518 from the image-residue evaluator identifying the image-residue pair to add to the IST set 506 (FIG. 6, operation 614).

The method 600 identifies the residue in the image-residue pair 514 as the "remaining data component" (FIG. 6, operation 616). The method 600 loops over the remaining signals in the reference set 504 (FIG. 6, operation 618). When all of the signals in the reference set 504 have been processed by the system 500 and method 600, the IST set 506 is complete.

Additional processing may be performed on an IST set (such as the IST set 306 of FIG. 3 or the IST set 506 of FIG. 5) once the IST set has been generated. For example, referring to FIG. 7, a dataflow diagram is shown of a system 700 for identifying one or more irreducible decomposition sets of ISTs for at least one first IST in an IST set, such as the IST set 306 of FIG. 3 or the IST set 506 of FIG. 5, according to one embodiment of the present invention. Referring to FIG. 8, a flowchart is shown of a method 800 that is performed by the system 700 of FIG. 7 according to one embodiment of the present invention. The system 700 and method 800 may be applied, for example, after the system 300 and method 400 of FIGS. 3-4 have been applied, or after the system 500 and 600 of FIGS. 5-6 have been applied.

Figure 7:
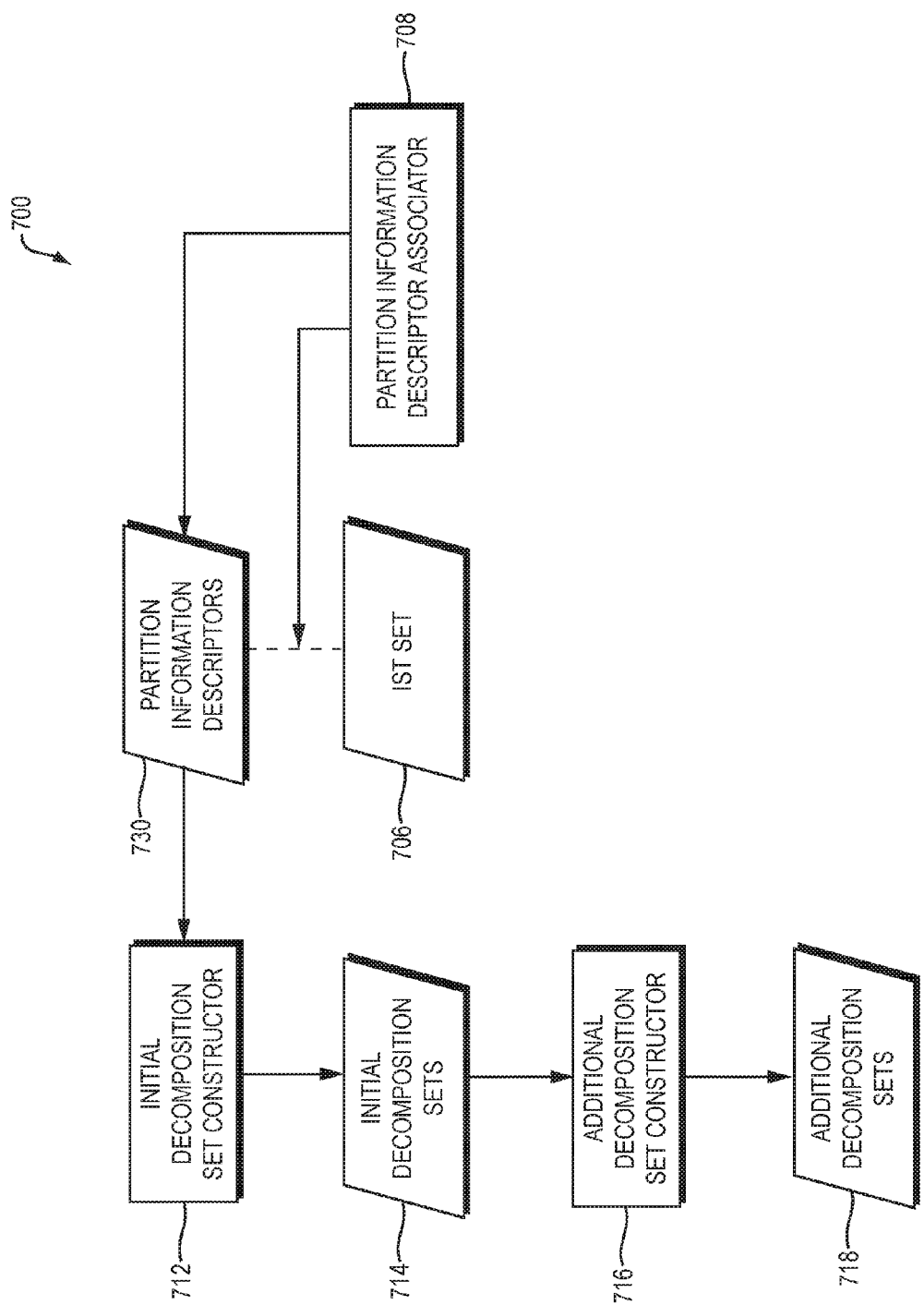
FIG. 7 is a dataflow diagram of a system for identifying one or more irreducible decomposition sets of ISTs for at least one first IST in an IST set, according to one embodiment of the present invention.
Figure 8:
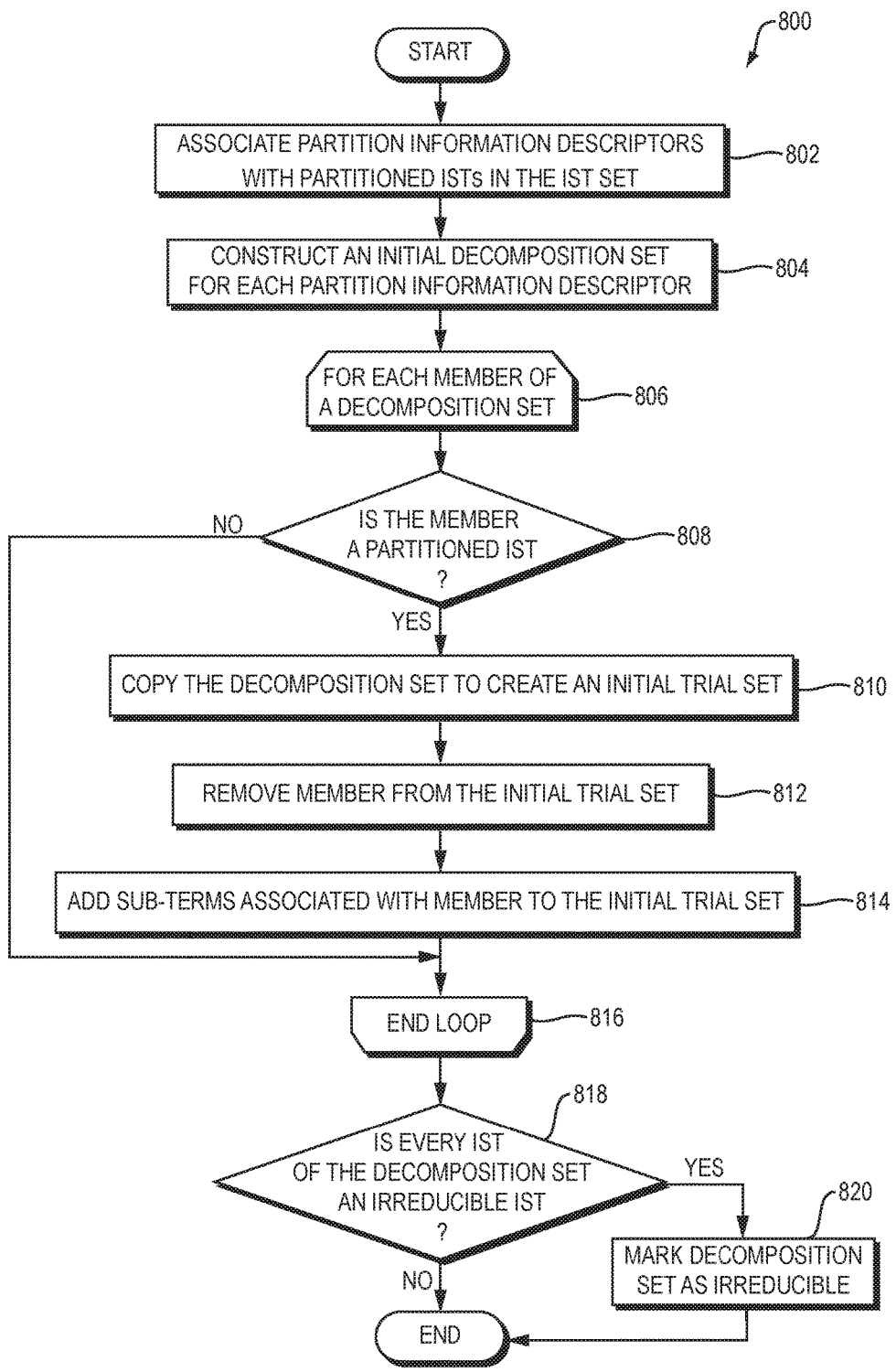
FIG. 8 is a flowchart of a method that is performed by the system of FIG. 7 according to one embodiment of the present invention.

In general, the system 700 and method 800 of FIGS. 7 and 8 augment the systems and methods of FIGS. 3-6 to identify decomposition sets for one or more of the ISTs in the IST set (e.g., the IST set 306 or the IST set 506), including the data signal itself (e.g., the data signal 302 or the data signal 502). Each decomposition set is associated with an IST in an IST set. An IST may have more than one decomposition set associated with it. In general, a decomposition set is a set of ISTs (in an IST set) which, when added together, equal the IST the IST set is associated with. Note that only partitioned ISTs have non-empty decomposition sets associated with them.

Referring to FIG. 7, the system 700 includes an IST set 706. As described in more detail below, the system 700 and method 800 of FIGS. 7 and 8 may be integrated with the system 300 and method 400 of FIGS. 3 and 4, or the system 500 and method 600 of FIGS. 5 and 6. The method 800 associates, with each of one or more partitioned ISTs in the IST set 706, a corresponding partition information descriptor (FIG. 8, operation 802). A partition information descriptor (also referred to herein as "partition information") may be any data that identifies a partitioning decomposition of a corresponding partitioned IST. The partition information descriptor specifies the image and residue, or the sub-terms, into which the corresponding partitioned IST can be decomposed. A partition information descriptor may be "associated" with a corresponding partitioned IST in any of a variety of ways, such as by storing data representing an association between the partition information descriptor and the corresponding partitioned IST.

The method 800 of FIG. 8 may associate the partition information descriptor with the corresponding partitioned IST during the construction of the IST set in the method 400 or 600 in response to such methods identifying a partitioning decomposition of the IST into: (1) an image and residue, or (2) a pair of sub-terms (e.g., in response to operation 412 in method 400 or in response to operation 610 in method 600).

Upon completion of the construction of the IST set 706 (e.g., after the completion of method 400 in FIG. 4 or the completion of method 600 in FIG. 6), an initial decomposition set constructor 712 constructs an initial decomposition set for each partition information descriptor associated with an IST in the IST set 706, thereby producing one or more initial decomposition sets 714 (FIG. 8, operation 804). The members of each of the initial decomposition sets 714 are the sub-terms specified in the corresponding partition information descriptor.

An additional decomposition set constructor 716 may iteratively construct one or more additional decomposition sets 718, based on an existing decomposition set (e.g., one of the initial decomposition sets 714), by scanning each of the members of the existing decomposition set. Recall that these members are also members of the IST set 706. For example, assume that the method 800 enters a loop over each member of a particular one of the initial decomposition sets 714 (FIG. 8, operation 806). When the additional decomposition set constructor 716 finds an IST that is a partitioned IST (FIG. 8, operation 808), the additional decomposition set constructor 716 constructs a trial set by: (1) copying the decomposition set to create an initial trial set (FIG. 8, operation 810); (2) removing the member (i.e., identified partitioned IST) from that trial set (FIG. 8, operation 812); and (3) adding the sub-ISTs identified by a partition information descriptor associated with the member (i.e., the just-removed partitioned IST) into the trial set, thereby producing the final value of the trial set (FIG. 8, operation 814). This trial set is a valid decomposition set for the IST associated with the existing decomposition set. If the trial set is not identical to a decomposition set already associated with that IST, then the method associates the trial set with that IST (such as by storing data representing an association between the trial set and the IST).

The method 800 determines whether every IST of the new decomposition set is an irreducible IST (FIG. 8, operation 818). If so, then the method 800 marks the new decomposition set as an irreducible decomposition set (FIG. 8, operation 820). Otherwise, the method 800 does not mark the new decomposition set as an irreducible decomposition set. Operations 808-814 may be repeated for all members of the decomposition set (FIG. 8, operation 816), potentially creating one new decomposition set for every member of the decomposition set being scanned that is a partitioned IST. Although not shown in FIG. 8, the loop represented by operations 806-820 may be applied iteratively to a plurality of decomposition sets, e.g., until all existing decomposition sets have been scanned without identifying any new decomposition sets.

Any of the methods disclosed herein for generating IST sets (such as the methods 400 and 600 of FIGS. 4 and 6, respectively), may be augmented to identify a base set for each of one or more of the ISTs in the IST set, including the data signal itself (e.g., the data signal 302 in FIG. 3 or the data signal 502 in FIG. 5). A base set is associated with a corresponding IST in the IST set, and is defined as the minimal subset of the reference set for which some linear mixture of the set members is the associated IST. Not all ISTs have non-empty base sets. For example, if an IST is only a residue of a partitioning decomposition, then that IST may be orthogonal to all of the signals in the reference set.

Each non-empty base set may or may not be a coherent base set. A coherent base set is a base set of an IST for which no linear mixture of the set members exists that is orthogonal to that IST. Only non-empty base sets can be coherent.

Figure 9:
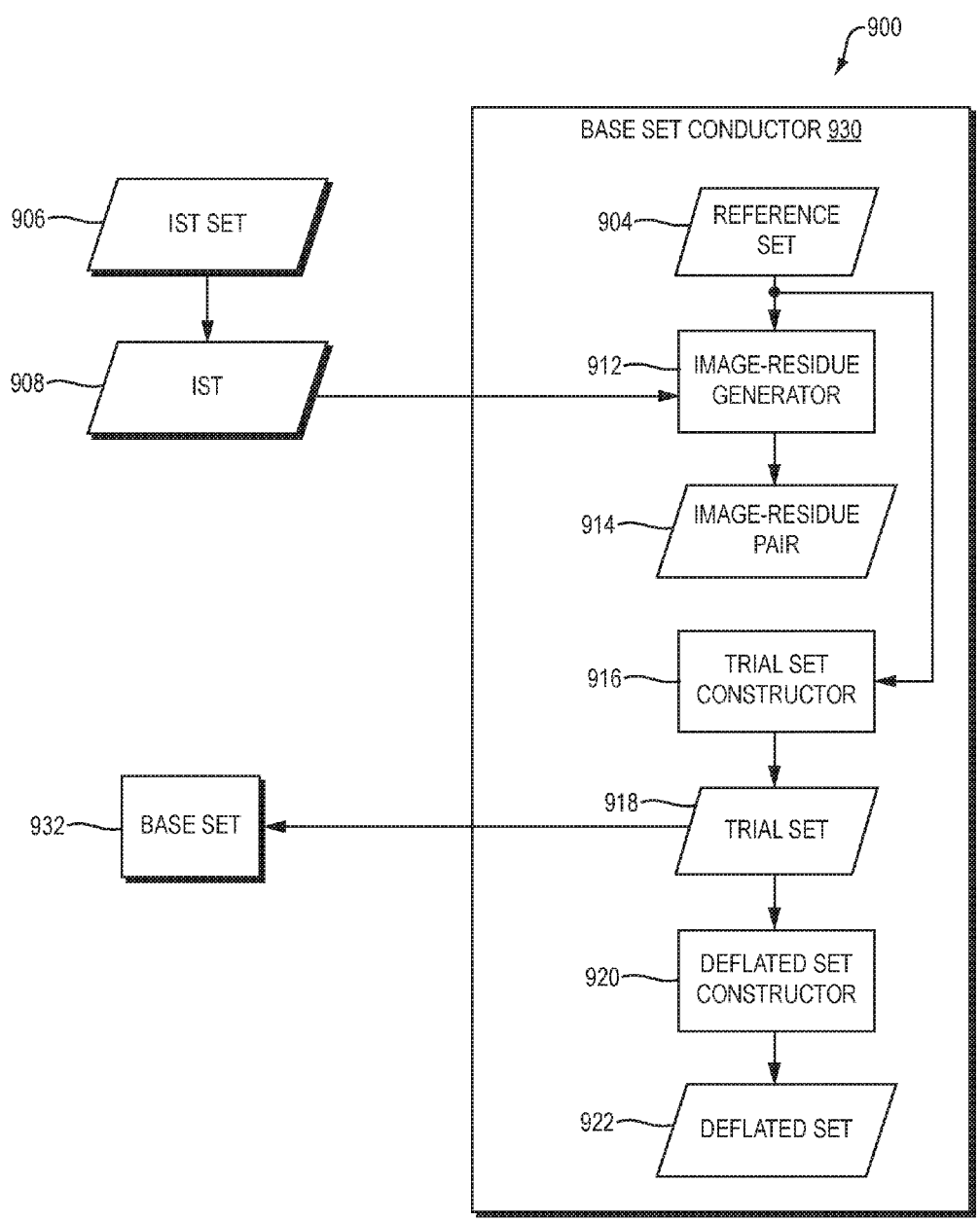
FIG. 9 is a dataflow diagram of a system for identifying one or more base sets for one or more ISTs in an IST set, according to one embodiment of the present invention.
Figure 10:
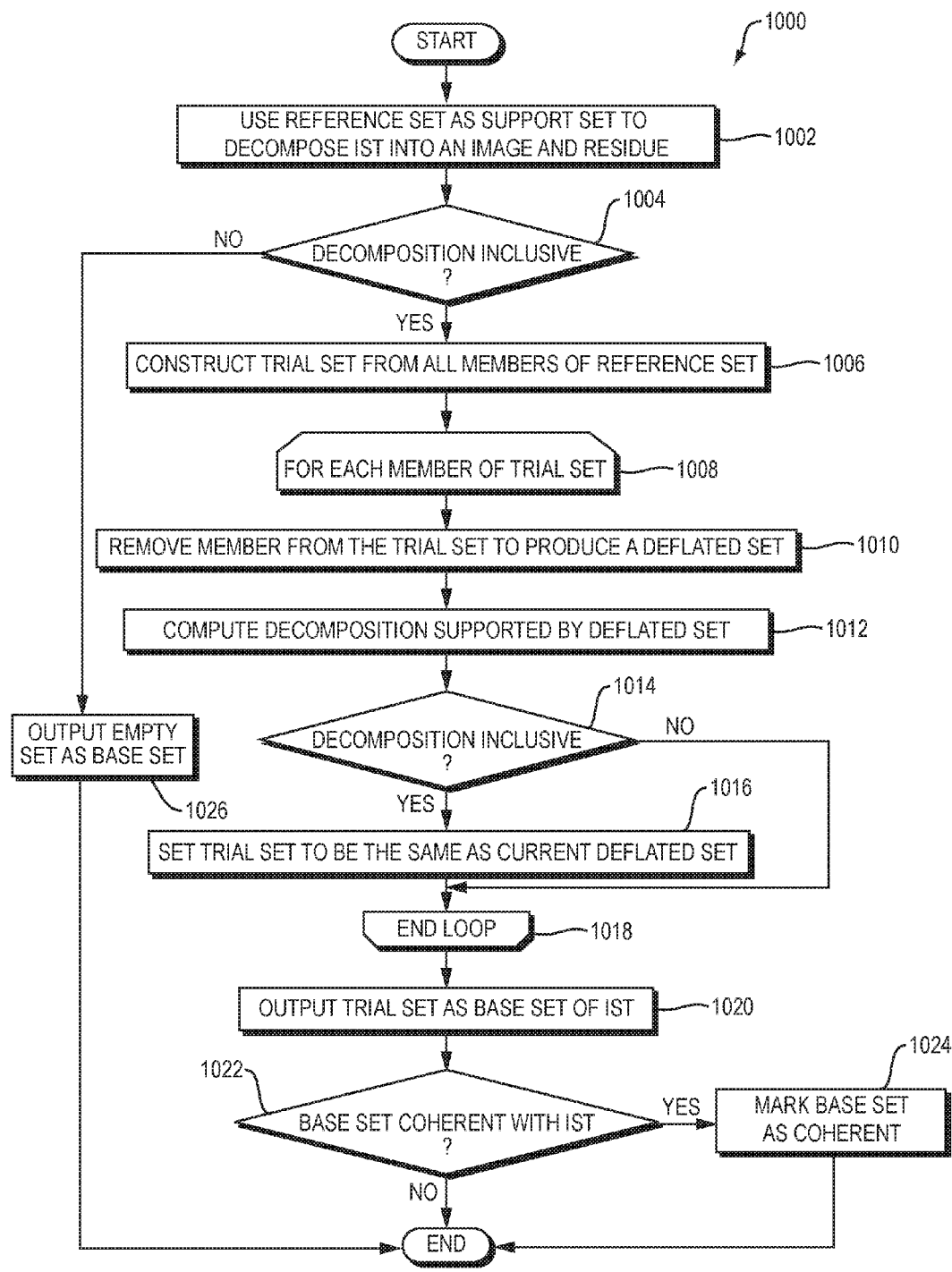
FIG. 10 is a flowchart of a method that is performed by the system of FIG. 9 according to one embodiment of the present invention.

For example, referring to FIG. 9, a dataflow diagram is shown of a system 900 for identifying one or more base sets for one or more ISTs in an IST set, according to one embodiment of the present invention. Referring to FIG. 10, a flowchart is shown of a method 1000 that is performed by the system 900 of FIG. 9 according to one embodiment of the present invention. The system 900 and method 1000 may be applied, for example, after the system 300 and method 400 of FIGS. 3-4 have been applied, or after the system 500 and 600 of FIGS. 5-6 have been applied.

In general, the system 900 and method 1000 may use a base set constructor 930 to construct a base set 932 for a corresponding IST 908 in an IST set 906 (which may, for example, be the IST set 306 of FIG. 3 or the IST set 506 of FIG. 5). Although only the single IST 908 and corresponding base set 932 are shown in FIG. 9, the base set constructor 930 may construct base sets 932 corresponding to any number of ISTs in the IST set 906 (e.g., all of the ISTs in the IST set 906).

An image-residue generator 312 uses the reference set 904 (which may, for example, be the reference set 304 of FIG. 3 or the reference set 504 of FIG. 5) as a support set to generate (e.g., compute) an image and residue pair 914 defined by that support set (i.e., reference set 904) on the IST 908, by performing a decomposition of the IST 908 based on that support set (i.e., reference set 904) into the image and residue 914 (FIG. 10, operation 1002). If the resulting decomposition is not inclusive, then the base set 932 for the IST 908 is the empty set, and is not coherent, in which case the base set constructor 930 outputs the empty set as the base set 932 (FIG. 10, operation 1026).

Otherwise, if the decomposition is inclusive, then a trial set constructor 916 constructs a trial set 918 containing all of the members of the reference set 904 (FIG. 10, operation 1006). A deflated set constructor 920 enters a loop over each member of the trial set 918 (FIG. 10, operation 1008). The deflated set constructor 920 scans the trial set 918, removing one reference signal from the trial set 918 at a time to produce a deflated set 922 (FIG. 10, operation 1010). The deflated set constructor 920 computes the decomposition supported by the deflated set 922 (FIG. 10, operation 1012). If that decomposition is inclusive (FIG. 10, operation 1014), then the members of the trial set 918 are set to be the same as those of the current deflated set 922 (FIG. 10, operation 1016), and scanning continues (FIG. 10, operation 1018). This deflation process continues until all the reference signals in the reference set 904 have been tested, and no signal in the trial set 918 can be removed from the trial set 918 without making the resulting decomposition non-inclusive.

The base set constructor 930 outputs the final trial set 918 (i.e., the trial set 918 after the result of operation 1012 is "no") as the base set 932 of the associated IST 908 (FIG. 10, operation 1020). Finally, if and only if all of the signals in the base set 932 are coherent with the corresponding IST 908 (FIG. 10, operation 1022), then the base set 932 is marked as coherent (FIG. 10, operation 1024).

Figure 11:
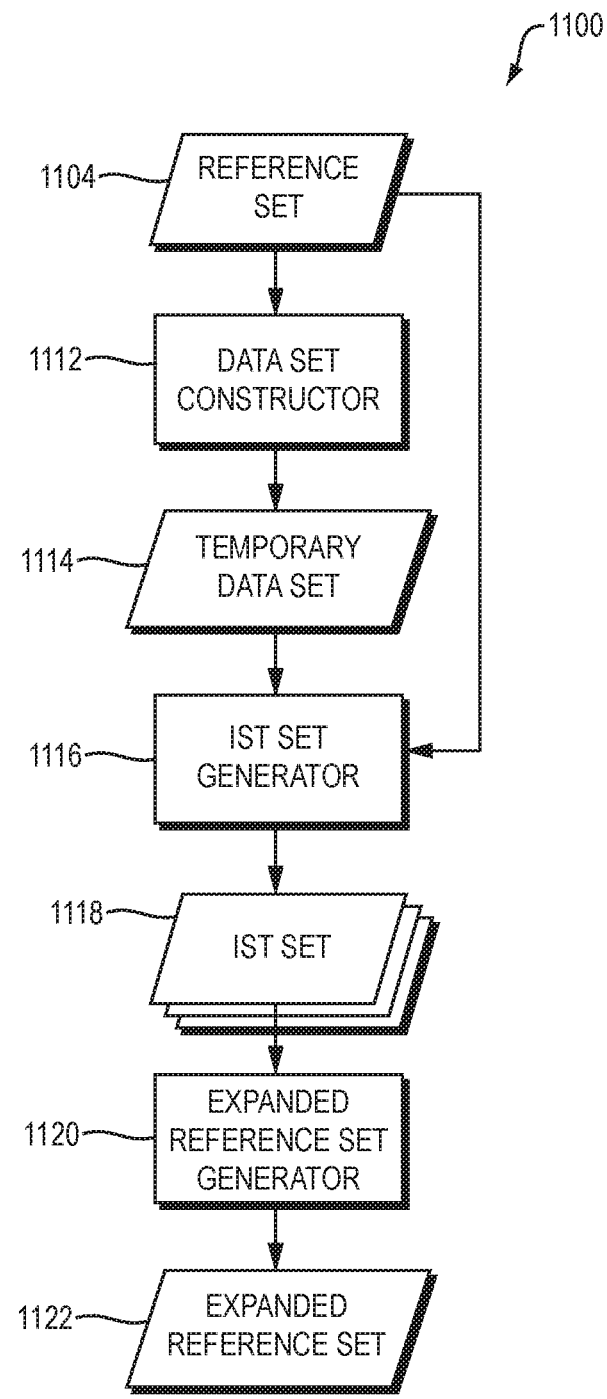
FIG. 11 is a dataflow diagram of a system for generating an expanded reference set for an arbitrary non-orthogonal reference set according to one embodiment of the present invention.

Embodiments of the present invention may be used advantageously to generate an expanded reference set from an arbitrary reference set by using signals in the reference set to decompose other signals, and by identifying members of the expanded reference set as all of the irreducible terms discovered through this decomposition of the reference set. Note that if all of the signals in a reference set are mutually orthogonal, the set is already maximally expanded. For non-orthogonal reference sets, the system 1100 of FIG. 11 and the method 1200 of FIG. 12 may be used to generate an expanded reference set from an arbitrary reference set.

Figure 12:
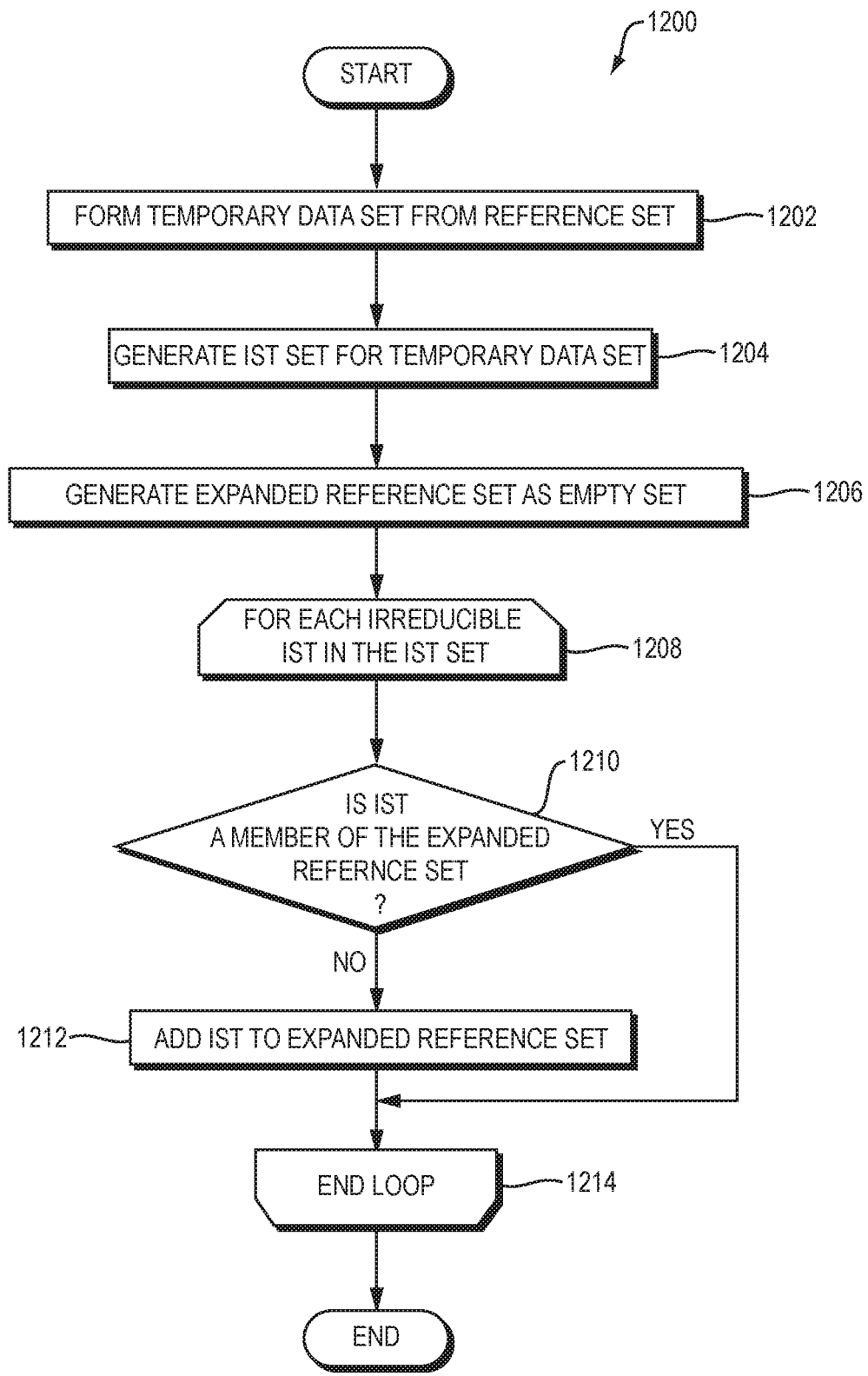
FIG. 12 is a flowchart of a method performed by the system of FIG. 11 according to one embodiment of the present invention.

A data set constructor 1112 forms a temporary data set 1114, whose members are all of the reference signals in a reference set 1104 (where the reference set may be any of the reference sets disclosed herein) (FIG. 12, operation 1202). An IST set generator 1116 generates a complete IST set 1118 for the temporary data set 1114 given the reference set 1104 (FIG. 12, operation 1204). More specifically, the IST set generator 1116 generates a plurality of IST sets, one for each data signal in the temporary data set 1114. The IST set 1118, therefore, includes that plurality of IST sets, or at least all of the members of that plurality of IST sets (which may be stored in a single set in the IST set 1118). An expanded reference set generator 1120 generates an expanded reference set 1122 as an empty set (FIG. 12, operation 1206).

The expanded reference set generator 1120 enters a loop over each irreducible IST in the IST set 1118 (FIG. 12, operation 1208). As mentioned above, the IST set 1118 may include IST members of a plurality of IST sets, one for each data signal in the temporary data set 1114. The expanded reference set generator 1120 determines whether that irreducible IST is a member of the expanded reference set 1122 (FIG. 12, operation 1210). If it is not, then the expanded reference set generator 1120 adds that irreducible IST to the expanded reference set 1122 (FIG. 12, operation 1212). Operations 1208 and 1210 are repeated for all remaining irreducible ISTs in the IST set 1118 (FIG. 12, operation 1214). The result of method 1200 is that the expanded reference set 1122 contains all of the irreducible ISTs from the IST set 1118.

Figure 13:
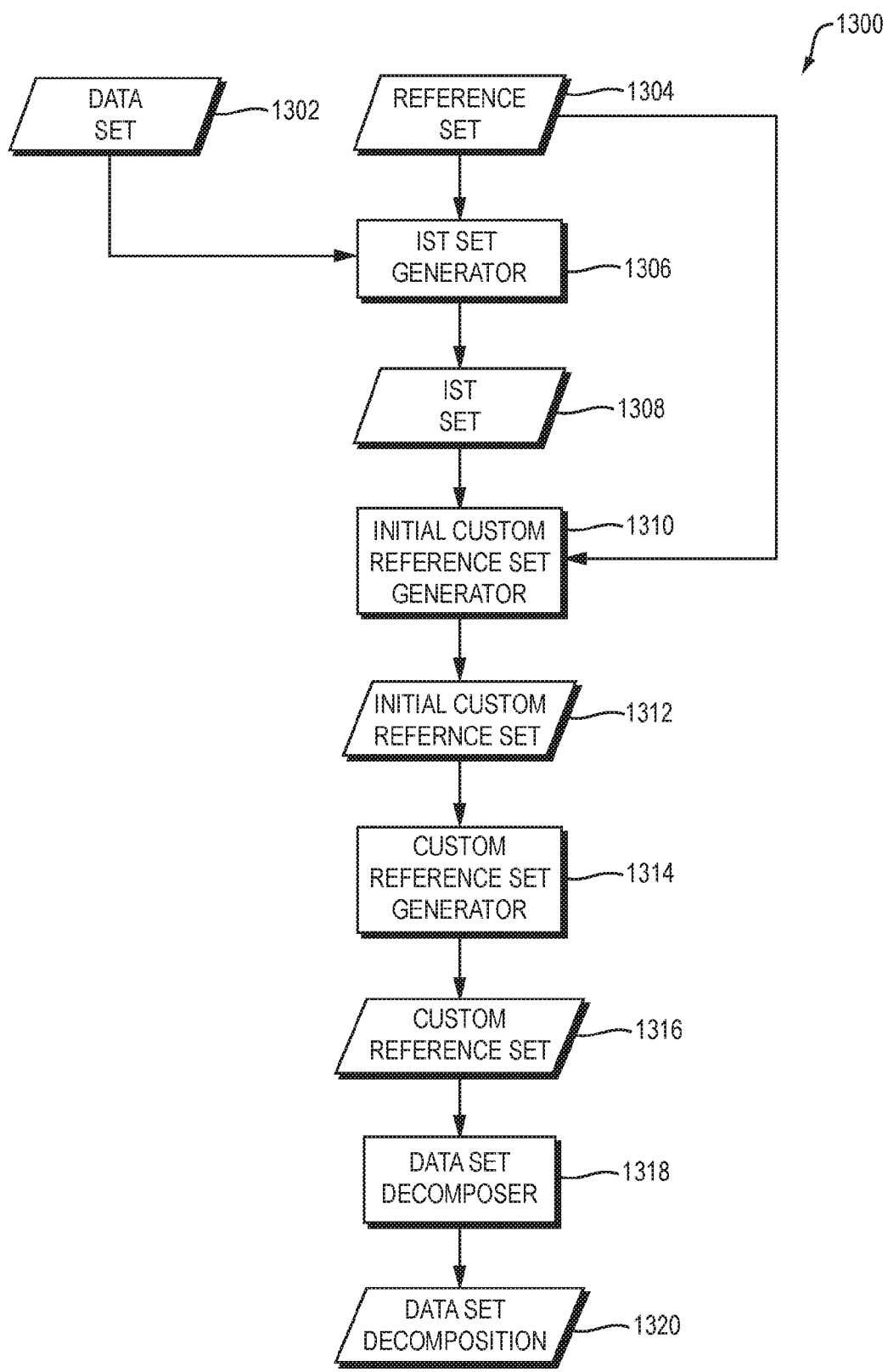
FIG. 13 is a dataflow diagram of a system for generating a custom reference set according to one embodiment of the present invention.
Figure 14:
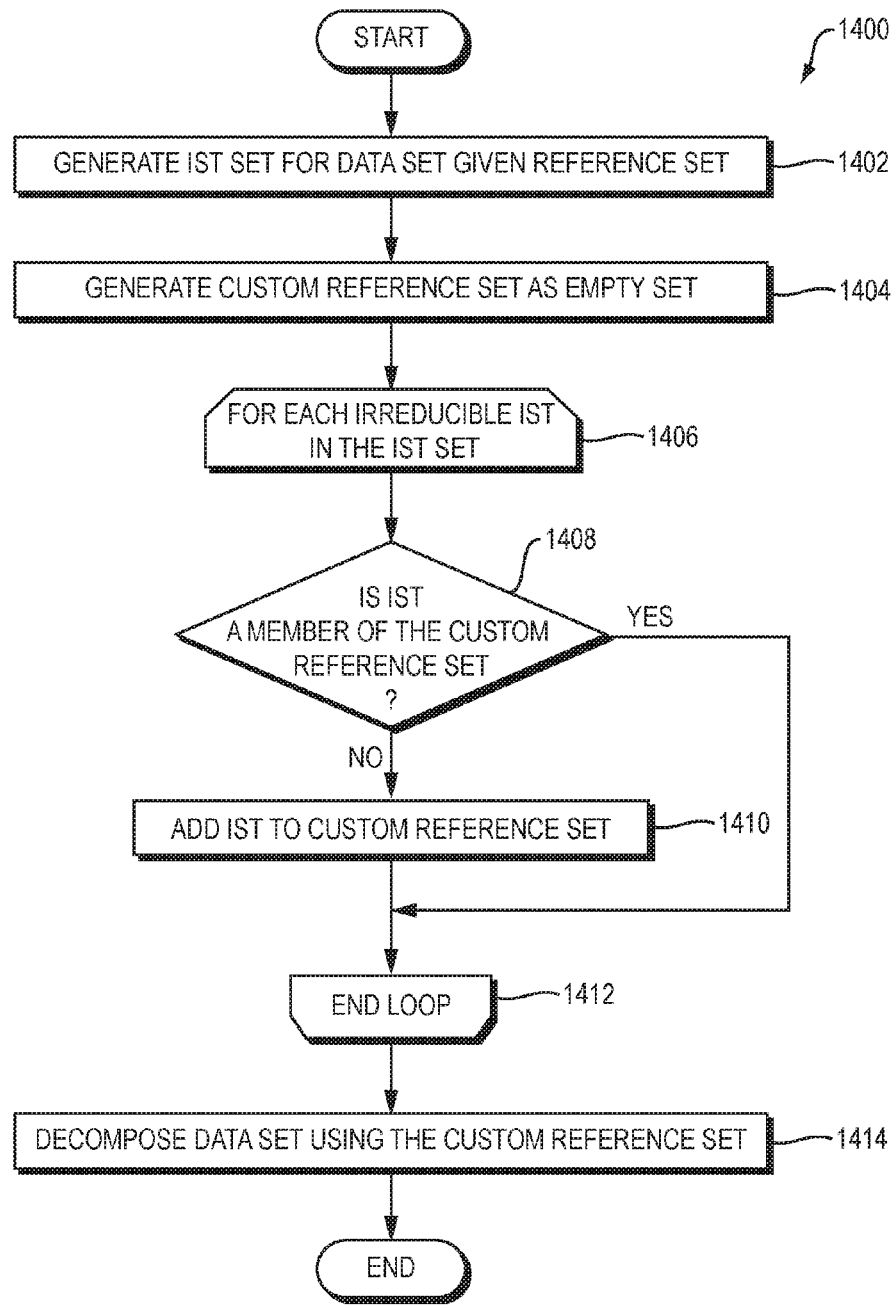
FIG. 14 is a flowchart of a method performed by the system of FIG. 13 according to one embodiment of the present invention.

Embodiments of the present invention may be used advantageously to generate a custom reference set for a particular data set from an initial reference set, by using signals in the initial reference set to decompose all of the data signals, and identifying members of the custom reference set as all of the irreducible ISTs of all of the IST sets for all of the signals in the data set. FIG. 13 shows a dataflow diagram of a system 1300 for generating such a custom reference set according to one embodiment of the present invention. FIG. 14 shows a flowchart of a method 1400 performed by the system 1300 of FIG. 13 according to one embodiment of the present invention.

An IST set generator 1306 generates an IST set 1308 for all of the data signals in a data set 1302 given a reference set 1304 (FIG. 14, operation 1402). More specifically, the IST set generator 1306 generates a plurality of IST sets, one for each data signal in the data set 1302. The IST set 1308, therefore, includes that plurality of IST sets, or at least all of the members of that plurality of IST sets (which may be stored in a single set in the IST set 1308). The reference set 1304 may be empty—that is, initially there may be no identified reference signals. An initial custom reference set generator 1310 generates an initial custom reference set 1312 as an empty set (FIG. 14, operation 1404).

The custom reference set generator 1314 enters a loop over each irreducible IST in the IST set 1308 (FIG. 14, operation 1406). As mentioned above, the IST set 1308 may include IST members of a plurality of IST sets, one for each data signal in the temporary data set 1114. The custom reference set generator 1314 determines whether that irreducible IST is a member of the custom reference set 1316 (which, initially, is the initial custom reference set 1312) (FIG. 14, operation 1408). If it is not, then the custom reference set generator 1314 adds that irreducible IST to the custom reference set 1316 (FIG. 14, operation 1410). Operations 1408 and 1410 are repeated for all remaining irreducible ISTs in the IST set 1308 (FIG. 14, operation 1412). The result of method 1400 is that the custom reference set 1316 contains all of the irreducible ISTs from the IST set 1308. Once the custom reference set has been created, a data set decomposer 1318 may advantageously use that custom reference set 1316 to decompose the data set 1302 from which the custom reference set 1316 was created into a decomposition 1320 (FIG. 14, operation 1414).

Figure 15:
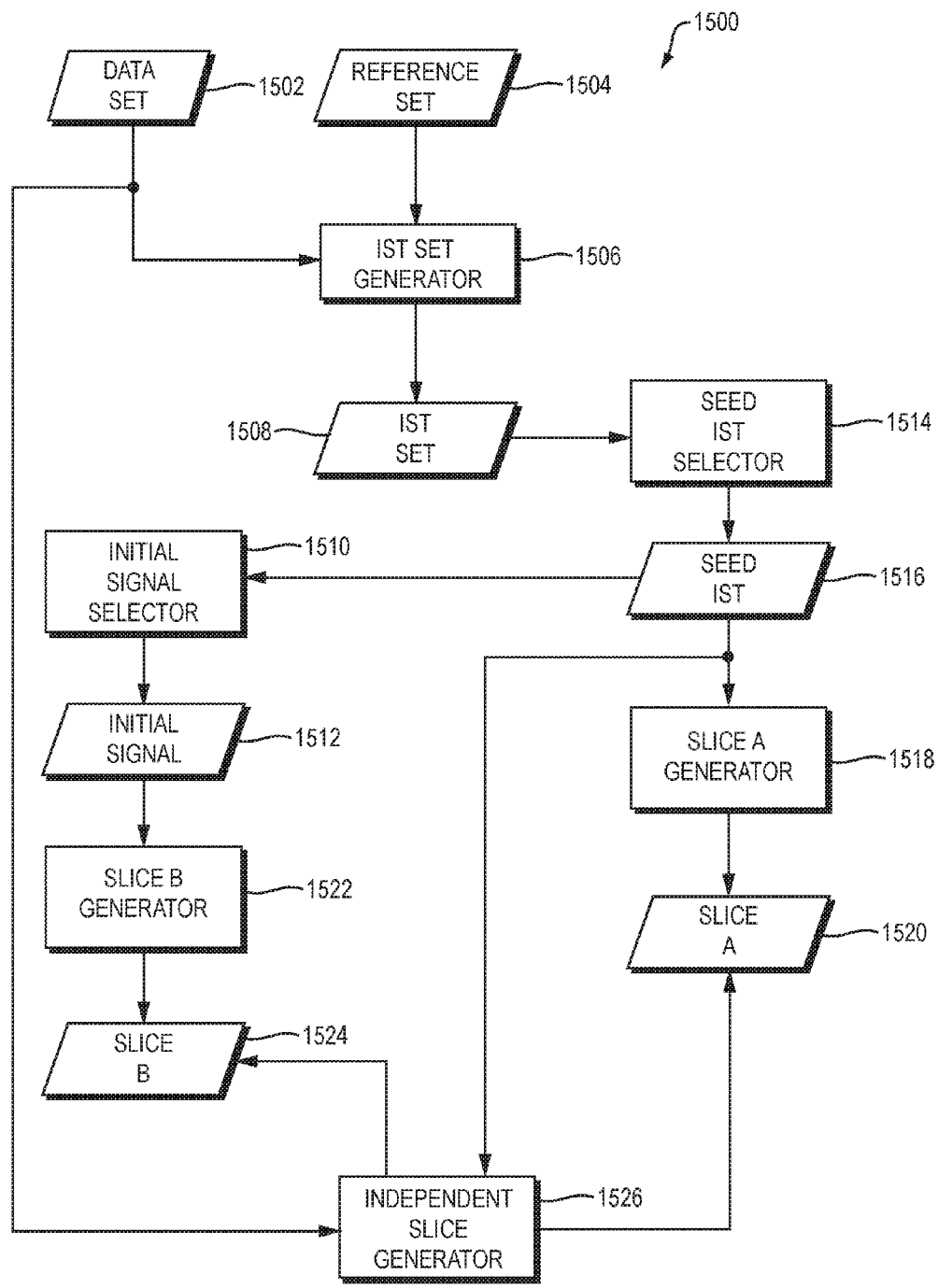
FIG. 15 is a dataflow diagram of a system for generating independent slices of data sets according to one embodiment of the present invention.
Figure 16A:
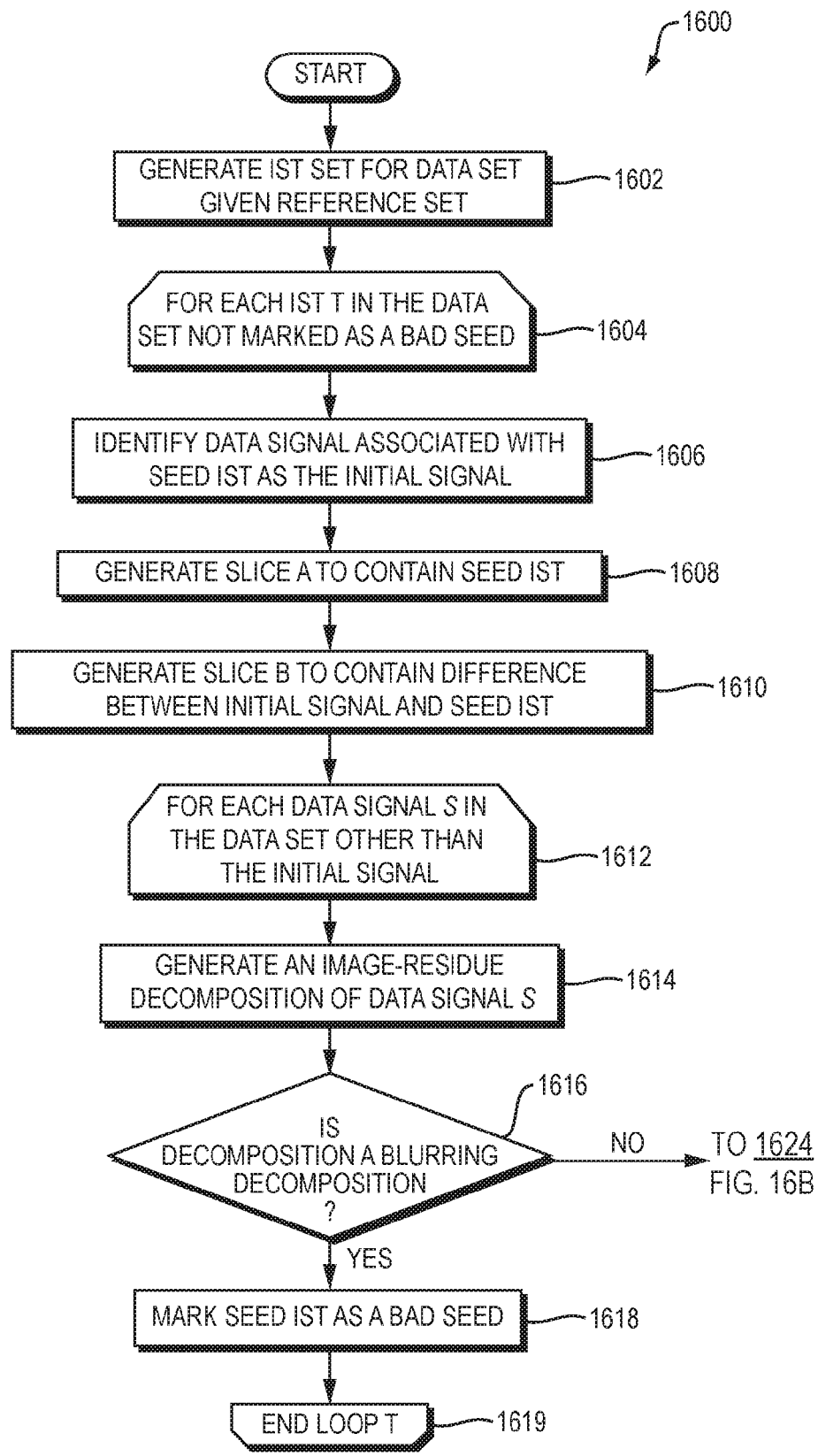
FIGS. 16A-16B are flowcharts of a method performed by the system of FIG. 15 according to one embodiment of the present invention.
Figure 16B:
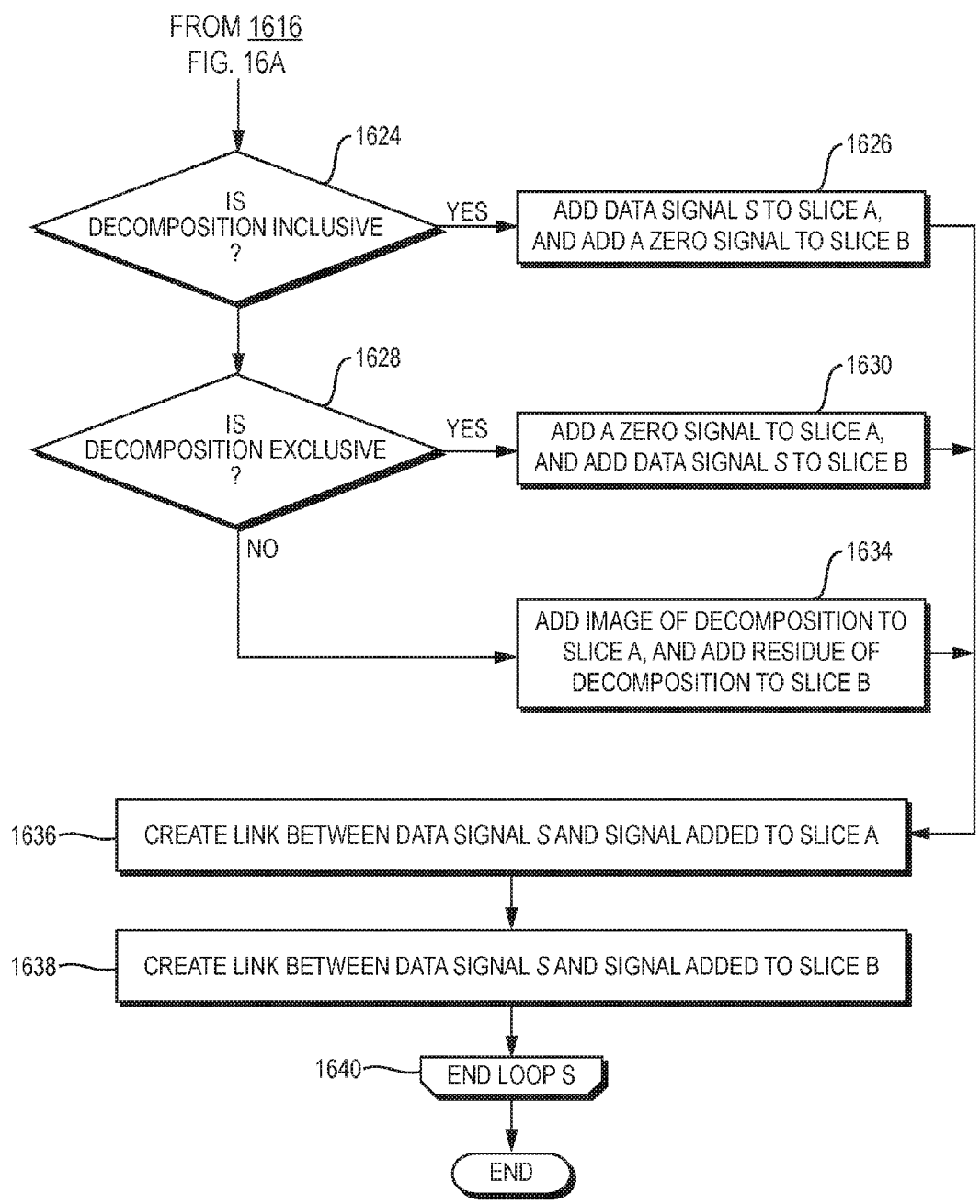

Referring to FIG. 15, a dataflow diagram is shown of a system 1500 for generating independent slices of data sets according to one embodiment of the present invention. Referring to FIGS. 16A-16B, flowcharts are shown of a method 1600 performed by the system 1500 of FIG. 15 according to one embodiment of the present invention.

An independent signal term (IST) generator 1506 generates an IST set 1508 for all of the data signals in a data set 1502 given a reference set 1504 (FIG. 16A, operation 1602). A seed IST selector 1514 enters a loop over all ISTs T in the data set 1502 which have not been marked as a "bad seed" (FIG. 16A, operation 1604). Any IST may be selected from the IST set 1508, in any order, as the seed IST. The current IST T is designated as a "seed IST." An initial signal selector 1510 selects a data signal associated with the seed IST 1516 as an initial signal 1512 (FIG. 16A, operation 1606).

A first slice generator 1518 generates a first slice 1520 (also referred to herein as "Slice A") containing the seed IST 1516 as its only member, and creates a link between that member and the initial signal 1512 (FIG. 16A, operation 1608). A second slice generator 1522 generates a second slice 1524 (also referred to herein as "Slice B") containing the difference between the initial signal 1512 and the seed IST 1516 as its only member, and creates a link between that member and the initial signal 1512 (FIG. 16A, operation 1610). The links generated in operations 1608 and 1610 may be implemented in any way, such as by data stored in a non-transitory computer-readable medium representing the link. The same is true of any link disclosed herein.

An independent slice generator 1526 enters a loop over each data signal S in the data set 1502, other than the initial signal 1512 (FIG. 16A, operation 1612). Treating slice A 1520 as a reference set, the independent slice generator 1526 generates an image-residue decomposition of data signal S (FIG. 16A, operation 1614).

The independent slice generator 1526 determines whether the decomposition performed in operation 1614 is a blurring decomposition (FIG. 16A, operation 1616). If it is, then no independent slice can be formed beginning with the seed IST 1516, in which case the current seed IST 1516 is marked as a "bad seed" (FIG. 16A, operation 1618), and the method 1600 continues to iterate over ISTs in the data set 1502 (FIG. 16A, operation 1619).

If the decomposition performed in operation 1614 is not a blurring composition, then the method 1600 continues to operation 1624 in FIG. 16B. If the decomposition performed in operation 1614 is inclusive (FIG. 16B, operation 1624), then the independent slice generator 1526 adds data signal S to slice A 1520, and adds a zero signal to slice B 1524 (FIG. 16B, operation 1626). If the decomposition performed in operation 1614 is exclusive (FIG. 16B, operation 1628), then the independent slice generator 1526 adds a zero signal to slice A 1520, and adds data signal S to slice B 1524 (FIG. 16B, operation 1630). If the decomposition performed in operation 1614 is not exclusive (FIG. 16B, operation 1628), then the decomposition performed in operation 1614 must be partitioning, and the independent slice generator 1526 adds the image of that decomposition to slice A 1520, and adds the residue of that decomposition to slice B 1524 (FIG. 16B, operation 1634).

The independent slice generator 1526 creates a link between the signal that was just added to slice A 1520 (i.e., in operation 1626, 1630, or 1634) and data signal S (FIG. 16B, operation 1636). The independent slice generator 1526 creates a link between the signal that was just added to slice B 1524 (i.e., in operation 1626, 1630, or 1634) and data signal S (FIG. 16B, operation 1638). The method 1600 repeats operations 1606-1638 for the remaining data signals in the data set 1502 other than the initial signal 1512 (FIG. 16B, operation 1640). If none of the data signals S resulted in a blurring decomposition, then the method 1600 ends upon completion of operation 1640.

It may be advantageous to use the image of some reference signal selected from the reference set 1504 as the seed IST 1516 that guides the decomposition of the data set 1502 into independent slices (e.g., slices A 1520 and B 1524). After the initial decomposition of the data set 1502 into two independent slices 1520 and 1524 (e.g., after completion of the method 1600 of FIGS. 16A-16B), embodiments of the present invention may form additional slices (not shown) by iteratively decomposing either or both of the initial independent slices 1520 and 1524 further. To do so, embodiments of the present invention may treat any existing slice to be decomposed (e.g., slice 1520 or 1524) as a data set, and apply the method 1600 of FIGS. 16A-16B to decompose that data set into two further slices.

Figure 17:
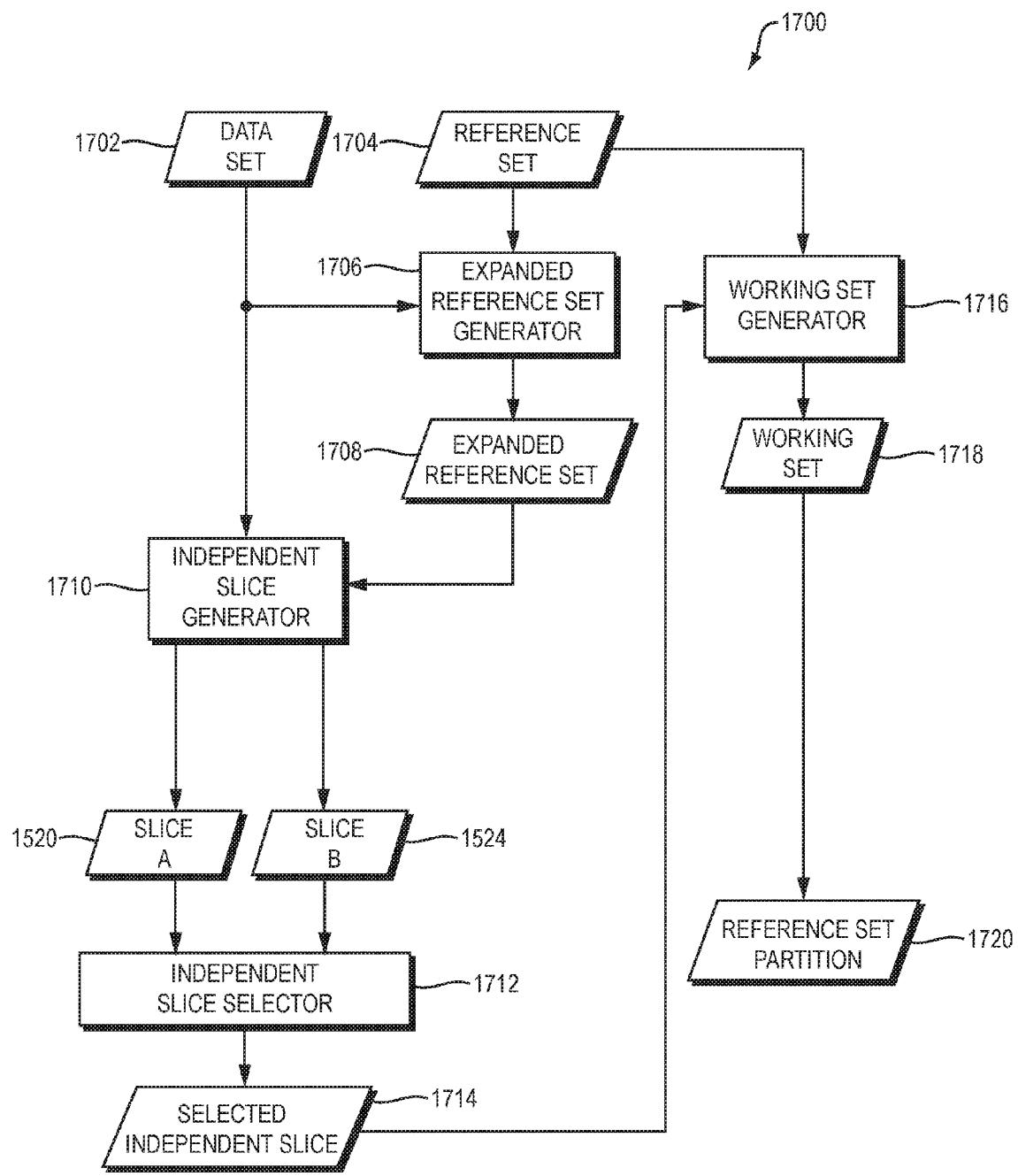
FIG. 17 is a dataflow diagram of a system for constructing a reference set partition for an independent slice of a data set according to one embodiment of the present invention.
Figure 18:
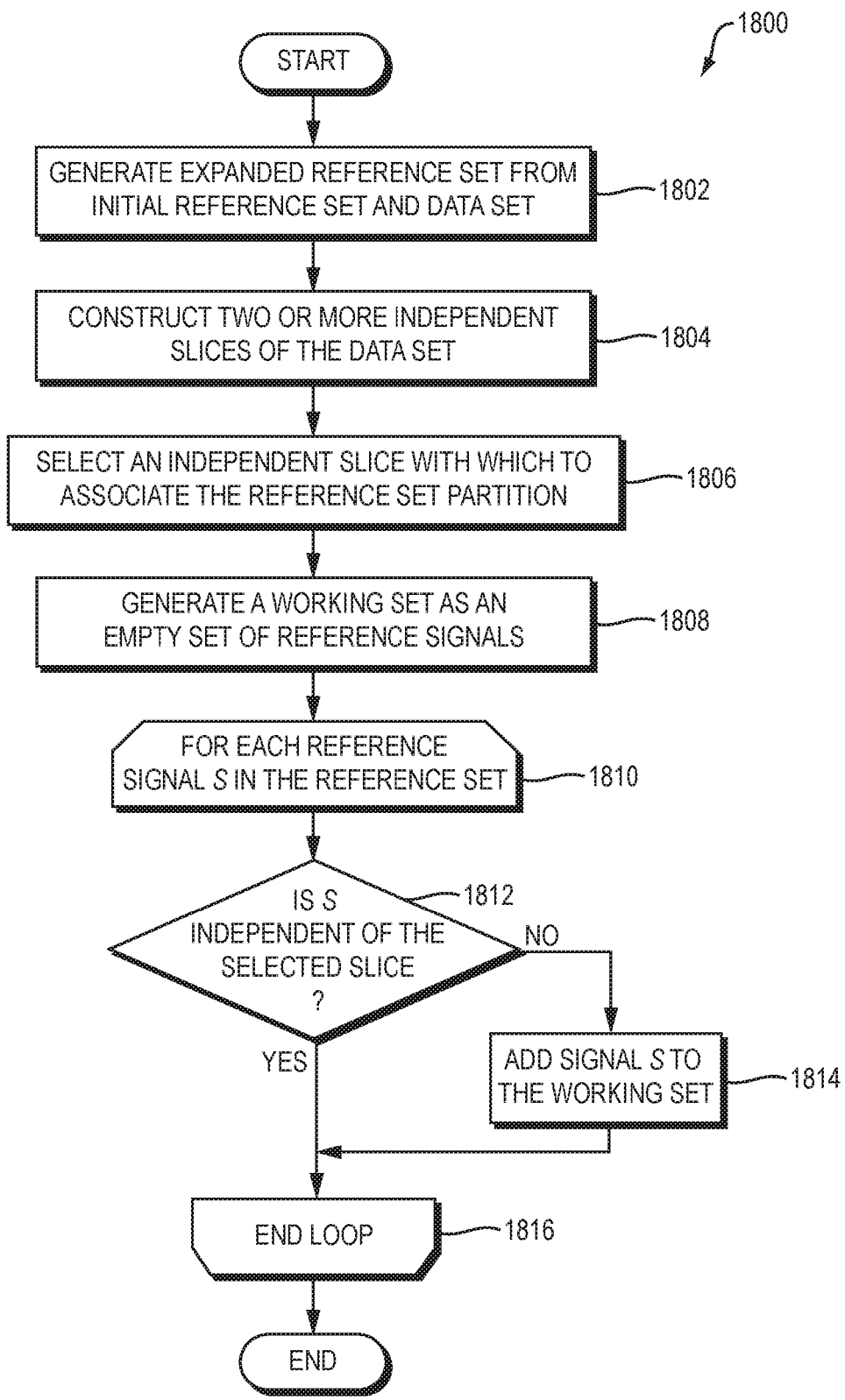
FIG. 18 is a flowchart of a method performed by the system of FIG. 17 according to one embodiment of the present invention.

Referring to FIG. 17, a dataflow diagram is shown of a system 1700 for constructing a reference set partition 1720 for an independent slice of a data set 1702 (such as any of the slices 1520 and 1524 generated in the system 1500 of FIG. 15) according to one embodiment of the present invention. Referring to FIG. 18, a flowchart is shown of a method 1800 performed by the system 1700 of FIG. 17 according to one embodiment of the present invention.

In the particular example shown in FIG. 17, the slice that is used to generate the reference set partition 1720 is slice A 1520 from FIG. 15. This is merely an example, however, and does not constitute a limitation of the present invention. Any independent slice of the data set 1702 may be used to generate the reference set partition 1720. The partition 1720 is a supporting set of reference signals for all of the non-zero members of the independent slice 1520 that is used to generate the reference set partition 1720.

An expanded reference set generator 1706 generates an expanded reference set 1708 from an initial reference set 1704 and a data set 1702, using any techniques disclosed herein (FIG. 18, operation 1802). Although not shown in FIGS. 17 and 18, the expanded reference set generator may also generate a custom reference set from the initial reference set 1704 and the data set 1702, using any techniques disclosed herein.

An independent slice generator 1710 generates at least two independent slices 1520 and 1524 of the data set 1702 (FIG. 18, operation 1804). The independent slice generator 1710 may use any of the techniques disclosed herein (e.g., in connection with FIGS. 15 and 16A-16B) to generate the independent slices 1520 and 1524. For that reason, the operation of independent slice generator 1710 is not shown in detail in FIG. 17.

An independent slice selector 1712 selects one of the generated independent slices 1520 and 1524 with which to associate a reference set partition, represented in FIG. 17 as the selected independent slice 1714 (FIG. 18, operation 1806). Assume, for purposes of example, that slice A 1520 is the selected independent slice 1714. Note that the output need not itself be a slice, but instead may be a pointer or other data indicating which of the independent slices 1520 and 1524 has been selected.

A working set generator 1716 generates a working set 1718 as an empty set of reference signals (FIG. 18, operation 1808). The working set generator 1716 enters a loop over each reference signal S in the reference set (FIG. 18, operation 1810). The working set generator 1716 determines whether reference signal S is independent of the selected slice 1714 (FIG. 18, operation 1812). If the signal S is not independent of the selected slice, then the working set generator 1716 adds signal S to the working set 1718 (FIG. 18, operation 1814). The working set generator 1716 repeats operations 1812-1814 for the remaining reference signals in the reference set 1704 (FIG. 18, operation 1816).

When all reference signals in the reference set have been considered, the working set generator 1716 associates the final working set 1718 with the selected slice 1714 as its reference set partition 1720 (FIG. 18, operation 1818).

As explained above, when multiple microphones are present in a complex acoustic environment with multiple simultaneously active sound sources, each microphone's response is, in general, the sum of that microphone's response to each of the active sound sources in isolation: the sum of its "solo response" to each source if all of the other sources were mute. Embodiments of the present invention may recover these solo responses by reconstructing them from the available microphone responses to all of the active sources "in concert."

The techniques described herein may be used to achieve this end, by assuming that the acoustic signals radiated by the sound sources are mutually statistically independent. In that case, the microphone signals can be considered to be data signals whose independent signal terms are the desired solo responses.

To reconstruct these solo responses, the actual microphone responses are digitized and processed as a set of data signals. A set of reference signals is generated by also processing the microphone signals using a blind source separation (BSS) process. The outputs of this BSS process are a set of signals, each of which is an arbitrarily filtered version of the acoustic signal generated by one of the sound sources. (Note that in general none of these signals will be any of the desired microphone solo responses.) The outputs of the blind source separation process are employed as a set of mutually independent reference signals.

Because the reference signals are considered to be statistically independent, the alternative method described above can be employed to generate IST sets by decomposing the data set of microphone signals using the reference set of source signals. This decomposition process will produce, among other things, irreducible ISTs each of which is the solo response of some microphone to some acoustic source.

The solo response of a particular microphone to a particular acoustic source can be identified using the BSS output that is a filtered version of that source's signal. To do so, the independent data slices of the data set, and their associated reference set partitions, are identified. Each of the reference set partitions will be a single BSS output signal, because those signals, at convergence, are mutually independent. Thus, each independent slice will have a reference set partition that is a single one of the filtered acoustic signals. Each slice is thus associated with a single acoustic source. Each IST in a slice is associated with a data signal, which in turn is the response signal from a particular microphone. Therefore each IST signal is the solo response of the microphone associated with that data signal to the acoustic source associated with the slice.

Embodiments of the present invention have a variety of advantages, such as the following. Many real-world sensors, such as microphones or bio-electrical sensors, are placed in environments characterized by multiple simultaneously active sources, and their response signals, at any given moment, are often the sum of what their responses would be to each individual source. Output signals generated by electrical or computational equipment may also take the form of a sum of independent terms, each of which is some unknown filtered version of an unknown signal generated by independent signal source or generator.

It is often of great interest to determine what the sensor or output signals would be if only a single source were active. However, it is typically not possible to arrange for all but one source to become inactive, so as to actually generate the desired "solo response" from the sensors or the equipment. It would be advantageous to be able to determine those solo responses by appropriately processing the actual sensor or output signals, comprising as they do the summed responses to the individual sources. Embodiments of the present invention include methods and systems for advantageously determining those solo responses. In certain aspects, embodiments of the present invention make use of information and assumptions about the desired solo responses (such as the assumption that they are statistically independent of each other), and of possibly-available reference signals that are known or thought to be arbitrary linear mixtures of the underlying signal sources.

For example, a particular method which may be performed by embodiments of the present invention is one in which each of a plurality of microphones in an environment with multiple simultaneously active acoustic sources responds with a signal equal to that microphone's response to each individual active source, summed over all the active sources. The microphone signals are digitized and processed by a blind source separation algorithm, each of whose outputs, upon convergence, is an approximately statistically independent filtered version of one of the acoustic source signals. The responses of each one of the set of microphones to a single acoustic source is reconstructed by: (a) designating the set of microphone responses as a set of data signals; (b) designating the set of blind source separation output signals as a set of reference signals; (c) computing the IST set for each of the data signals in the data set using the reference set; (d) identifying each irreducible IST of a data signal as the response of the microphone associated with the data signal to some one acoustic source in isolation; (e) computing each independent slice of the data set that has a non-empty associated reference set partition; (f) identifying each such independent slice with the acoustic source, a filtered version of whose signal appears as the sole signal in the reference set partition of the independent slice; and (g) identifying each IST in those independent slices with the microphone whose signal is the IST's data signal.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Any reference herein to "associating" one unit of data with another may be implemented, for example, by storing data, in a non-transitory computer readable medium, representing the association between the two units of data. A variety of techniques for representing such associations are well-known to those having ordinary skill in the art. Similarly, any reference herein to "marking" a unit of data with a property may be implemented, for example, by storing data, in a non-transitory computer readable medium representing the property and indicating that the property is associated with the unit of data. A variety of techniques for performing such markings are well-known to those having ordinary skill in the art.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention process automatically (e.g., using electronic circuitry, such as one or more computer processors) signals (e.g., acoustic and/or electrical signals) that cannot be manipulated, understood, or otherwise processed manually by a human.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method performed by at least one computer processor executing computer program code embodied in at least one non-transitory computer-readable medium, the method comprising:
   (1) adding a data signal to an independent signal term (IST) set;

(2) constructing, based on a reference set, at least one support set;
(3) for each support set S in the at least one support set, generating a corresponding image-residue pair by performing a decomposition of the data signal, based on the support set S, into the corresponding image-residue pair;
(4) evaluating each image-residue pair generated in (3);
(5) determining whether, for each image-residue pair generated in (3), based on the evaluation of that image-residue pair in (4), the decomposition that generated the image-residue pair was a partitioning decomposition;
(6) adding each image-residue pair generated by each decomposition determined to be a partitioning decomposition in (5) to the IST set; and
(7) in response to determining that the image and residue in at least one of the image-residue pairs generated in (3) are independent of each other, labeling the data signal as a partitioned IST, thereby providing at least one partitioned IST in the IST set.

2. The method of claim 1, further comprising:
(8) finding at least one additional partitioning decomposition of ISTs in the IST set, comprising finding a first IST and a second IST in the IST set for which: (i) the first IST has at least as much power as the second IST; and (ii) the second IST is independent of a difference between the first IST and the second IST;
(9) labeling the first IST as a partitioned IST;
(10) labeling the second IST as a sub-IST of the first IST;
(11) adding a residue of a decomposition of the first IST by the second IST to the IST set, wherein the difference between the first IST and the second IST comprises the residue of the decomposition of the first IST by the second IST.

3. The method of claim 2, further comprising repeating (8)-(11) at least once.

4. The method of claim 1, further comprising:
(8) associating partition information with the at least one partitioned IST in the IST set, wherein said partition information identifies at least one partitioning decomposition of the at least one partitioned IST;
(9) identifying an image and residue of the at least one partitioning decomposition of the at least one partitioned IST; and
(10) identifying at least one decomposition set, the decomposition set comprising at least one image and residue of at least one partitioning decomposition of the at least one partitioned IST.

5. The method of claim 4, further comprising:
(11) identifying a member of the at least one decomposition set for which a partitioning decomposition has been identified;
(12) identifying a trial set comprising members of the at least one decomposition set for which a partitioning decomposition has been identified, minus the member identified in (11), plus first and second terms of the partitioning decomposition for the member identified in (11);
(13) if the trial set is not identical to a decomposition set identified in (10), then adding the trial set to the at least one decomposition set; and
(14) identifying a decomposition set, from the at least one decomposition set, in which all members are irreducible ISTs, as an irreducible decomposition set.

6. The method of claim 5, comprising repeating (11)-(14) to identify at least one additional irreducible decomposition set.

7. The method of claim 1, further comprising:
(8) associating a base set with a corresponding IST in the IST set, wherein the base set is a minimal subset of the reference set for which some linear mixture of the base set's members is the corresponding IST.

8. The method of claim 7, further comprising:
(9) determining whether the base set is a coherent base set by determining whether all members of the base set are coherent with the corresponding IST in the IST set.

9. The method of claim 1, wherein a data set comprises the data signal and at least one additional data signal, the method further comprising:
(8) identifying a first independent slice of the data set and a second independent slice of the data set;
wherein the first independent slice comprises a first set of signals, wherein the second independent slice comprises a second set of signals;
wherein each non-zero member of each of the first and second independent slices is orthogonal to every non-zero member of the other independent slice, and is either a member of the data set or a sub-IST of a member of the data set; and
wherein each data signal member of the data set either:
(a) is a unique member of one of the first independent slice and the second independent slice, the other independent slice containing a single corresponding zero signal; or
(b) is decomposed into independent sub-terms, each sub-IST being a unique member of a separate one of the first independent slice and the second independent slice, the remaining sub-IST each containing a single corresponding zero signal.

10. The method of claim 9, wherein at least one of the first independent slice and the second independent slice has associated with it a reference set partition, wherein the reference set partition is a supporting set of reference set members for all non-zero members of the at least one of the first independent slice and the second independent slice.

11. A system comprising at least one non-transitory computer-readable medium comprising computer program code executable by at least one computer processor to perform a method, the method comprising:
(1) adding a data signal to an independent signal term (IST) set;
(2) constructing, based on a reference set, at least one support set;
(3) for each support set S in the at least one support set, generating a corresponding image-residue pair by performing a decomposition of the data signal, based on the support set S, into the corresponding image-residue pair;
(4) evaluating each image-residue pair generated in (3);
(5) determining whether, for each image-residue pair generated in (3), based on the evaluation of that image-residue pair in (4), the decomposition that generated the image-residue pair was a partitioning decomposition;
(6) adding each image-residue pair generated by each decomposition determined to be a partitioning decomposition in (5) to the IST set; and
(7) in response to determining that the image and residue in at least one of the image-residue pairs generated in (3) are independent of each other, labeling the data signal as a partitioned IST, thereby providing at least one partitioned IST in the IST set.

12. The system of claim 11, wherein the method further comprises:

(8) finding at least one additional partitioning decomposition of ISTs in the IST set, comprising finding a first IST and a second IST in the IST set for which: (i) the first IST has at least as much power as the second IST; and (ii) the second IST is independent of a difference between the first IST and the second IST;

(9) labeling the first IST as a partitioned IST;

(10) labeling the second IST as a sub-IST of the first IST;

(11) adding a residue of a decomposition of the first IST by the second IST to the IST set, wherein the difference between the first IST and the second IST comprises the residue of the decomposition of the first IST by the second IST.

13. The system of claim 12, wherein the method further comprises repeating (8)-(11) at least once.

14. The system of claim 11, wherein the method further comprises:
(8) associating partition information with the at least one partitioned IST in the IST set, wherein said partition information identifies at least one partitioning decomposition of the at least one partitioned IST;
(9) identifying an image and residue of the at least one partitioning decomposition of the at least one partitioned IST; and
(10) identifying at least one decomposition set, the decomposition set comprising at least one image and residue of at least one partitioning decomposition of the at least one partitioned IST.

15. The system of claim 14, wherein the method further comprises:
(11) identifying a member of the at least one decomposition set for which a partitioning decomposition has been identified;
(12) identifying a trial set comprising members of the at least one decomposition set for which a partitioning decomposition has been identified, minus the member identified in (11), plus first and second terms of the partitioning decomposition for the member identified in (11);
(13) if the trial set is not identical to a decomposition set identified in (10), then adding the trial set to the at least one decomposition set; and
(14) identifying a decomposition set, from the at least one decomposition set, in which all members are irreducible ISTs, as an irreducible decomposition set.

16. The system of claim 15, wherein the method further comprises repeating (11)-(14) to identify at least one additional irreducible decomposition set.

17. The system of claim 11, wherein the method further comprises:
(8) associating a base set with a corresponding IST in the IST set, wherein the base set is a minimal subset of the reference set for which some linear mixture of the base set's members is the corresponding IST.

18. The system of claim 17, wherein the method further comprises:
(9) determining whether the base set is a coherent base set by determining whether all members of the base set are coherent with the corresponding IST in the IST set.

19. The system of claim 11, wherein a data set comprises the data signal and at least one additional data signal, and wherein the method further comprises:
(8) identifying a first independent slice of the data set and a second independent slice of the data set;
wherein the first independent slice comprises a first set of signals, wherein the second independent slice comprises a second set of signals;
wherein each non-zero member of each of the first and second independent slices is orthogonal to every non-zero member of the other independent slice, and is either a member of the data set or a sub-IST of a member of the data set; and
wherein each data signal member of the data set either:
(a) is a unique member of one of the first independent slice and the second independent slice, the other independent slice containing a single corresponding zero signal; or
(b) is decomposed into independent sub-terms, each sub-IST being a unique member of a separate one of the first independent slice and the second independent slice, the remaining sub-IST each containing a single corresponding zero signal.

20. The system of claim 19, wherein at least one of the first independent slice and the second independent slice has associated with it a reference set partition, wherein the reference set partition is a supporting set of reference set members for all non-zero members of the at least one of the first independent slice and the second independent slice.

* * * * *